US009416350B2

(12) United States Patent
Yoshida et al.

(10) Patent No.: US 9,416,350 B2
(45) Date of Patent: Aug. 16, 2016

(54) ENZYME FUNCTION MODIFICATION METHOD AND ENZYME VARIANT THEREOF

(75) Inventors: Shinichi Yoshida, Takasago (JP); Shunichi Taira, Takasago (JP); Masakatsu Nishihachijyo, Takasago (JP); Masutoshi Nojiri, Takasago (JP); Shigeru Kawano, Takasago (JP)

(73) Assignee: KANEKA CORPORATION, Osaka (JP)

( * ) Notice: Subject to any disclaimer, the term of this patent is extended or adjusted under 35 U.S.C. 154(b) by 0 days.

(21) Appl. No.: 14/129,834

(22) PCT Filed: Jun. 27, 2012

(86) PCT No.: PCT/JP2012/066418
§ 371 (c)(1),
(2), (4) Date: Mar. 28, 2014

(87) PCT Pub. No.: WO2013/002277
PCT Pub. Date: Jan. 3, 2013

(65) Prior Publication Data
US 2014/0256930 A1    Sep. 11, 2014

(30) Foreign Application Priority Data

Jun. 28, 2011 (JP) ................................. 2011-143423

(51) Int. Cl.
*C12N 9/04* (2006.01)
*C07H 19/207* (2006.01)
*C12P 19/36* (2006.01)

(52) U.S. Cl.
CPC ............ *C12N 9/0006* (2013.01); *C07H 19/207* (2013.01); *C12P 19/36* (2013.01); *Y02P 20/52* (2015.11)

(58) Field of Classification Search
CPC ...... C12N 9/0006; C12P 19/36; C07H 19/207
USPC ........ 536/26.24, 23.2; 435/190, 252.3, 254.2, 435/320.1, 325, 348, 412, 417, 419, 90
See application file for complete search history.

(56) References Cited

U.S. PATENT DOCUMENTS

| | | | |
|---|---|---|---|
| 5,334,507 A | 8/1994 | Soya et al. | |
| 5,763,236 A | 6/1998 | Kojima et al. | |
| 8,129,163 B2* | 3/2012 | Kawano et al. | 435/189 |
| 2003/0100065 A1 | 5/2003 | Hummel et al. | |
| 2004/0248250 A1 | 12/2004 | Nakai et al. | |
| 2007/0292923 A1 | 12/2007 | Iwasaki et al. | |
| 2008/0038803 A1 | 2/2008 | Iwasaki et al. | |
| 2010/0035317 A1 | 2/2010 | Kawano et al. | |
| 2013/0030164 A1* | 1/2013 | Yoshida et al. | 536/23.2 |

FOREIGN PATENT DOCUMENTS

| | | |
|---|---|---|
| CN | 101407780 B | 8/2010 |
| EP | 0 533 183 A2 | 3/1993 |
| EP | 0 645 453 A2 | 3/1995 |
| EP | 1 241 598 A1 | 9/2002 |
| EP | 2 096 165 A1 | 9/2009 |
| JP | 5-103697 A | 4/1993 |
| JP | 7-231785 A | 9/1995 |
| JP | 8-196281 A | 8/1996 |
| JP | 2003-116585 A | 4/2003 |
| JP | 2003-169696 A | 6/2003 |
| JP | 3574682 B2 | 10/2004 |
| JP | 2005-102511 A | 4/2005 |
| JP | 2005-533497 A | 11/2005 |
| WO | WO 03/004653 A1 | 1/2003 |
| WO | WO 2004/009807 A1 | 1/2004 |
| WO | WO 2006/013802 A1 | 2/2006 |
| WO | WO 2006/033333 A1 | 3/2006 |
| WO | WO 2006/090814 A1 | 8/2006 |
| WO | WO 2008/066018 A1 | 6/2008 |

OTHER PUBLICATIONS

Larroy et al. Characterization of a *Saccharomyces cerevisiae* NADP(H)-dependent alcohol dehydrogenase (ADHVII), a member of the cinnamyl alcohol dehydrogenase family. Eur J Biochem 269, 5738-5745, 2002.*
English translation of International Preliminary Report on Patentability and Written opinion mailed Jan. 16, 2014, in PCT International Application No. PCT/JP2012/066418.
Khoury et al., "Computational design of *Candida boidinii*xylose reductase for altered cofactor specificity," Protein Science (2009), vol. 18, pp. 2125-2138.
Machielsen et al., "Cofactor engineering of *Lactobacilus brevis* alcohol dehydrogenase by computational design," Eng. Life Sci. (2009), vol. 9, No. 1, pp. 38-44.
McKeever et al., "Amino acid substitution of arginine 80 and 17β-hydroxysteroid dehydrogenase type 3 and its effect of NADPH cofactor binding and oxidation/reduction kinetics," Biochimica et Biophysica Acta (2002), vol. 1601, pp. 29-37.
Nakanishi et al., "Switch of Coenzyme Specificity of Mouse Lung Carbonyl Reductase by Substitution of Theronine 38 with Aspartic Acid," J. Biol. Chem. (Jan. 24, 1997), vol. 272, No. 4, pp. 2218-2222.

(Continued)

*Primary Examiner* — Clinton Brooks
*Assistant Examiner* — Yih-Horng Shiao
(74) *Attorney, Agent, or Firm* — Birch, Stewart, Kolasch & Birch, LLP

(57) ABSTRACT

An object of the present invention is to provide a method for converting the coenzyme dependency of enzymes of the medium-chain dehydrogenase/reductase (MDR) family. A further object of the present invention is to provide enzyme variants of the MDR family whose coenzyme dependency is converted by the conversion method and a method for enzymatically producing optically active alcohols using the enzymes. The present inventors developed a novel enzyme conversion method for converting the coenzyme dependency of enzymes of the MDR family, rationally designed enzyme variants that are altered by the enzyme conversion method to be able to use NADPH as a coenzyme from a useful enzyme of the MDR family that uses NADH as a coenzyme, and actually provide variants having such an ability.

23 Claims, 1 Drawing Sheet

(56) References Cited

OTHER PUBLICATIONS

Penning, T. M. and J. M. Jez, "Enzyme Redesign," Chem. Rev. (2001), vol. 101, pp. 3027-3046.
Tanaka et al., "Crystal structure of the ternary complex of mouse lung carbonyl reductase at 1.8 A resolution: the structural origin of coenzyme specificity in the short-chain dehydrogenase/reductase family," Structure (Jan. 15, 1996), vol. 4, pp. 33-45.
Zhang et al., "Ser67Asp and His68Asp Substitutions in *Candida parapsifosis* Carbonyl Reductase After the Coenzyme Specificity and Enantioselectivity of Ketone Reduction," Applied and Environmental Microbiology (Apr. 2009), vol. 75, No. 7, pp. 2176-2183.
Serov et al., "Engineering of coenzyme specificity of formate dehydrogenase from *Saccharomyces cerevisiae*," Biochem. J. (2002), vol. 367, pp. 841-847.
Akada et al., "Construction of Recombinant Sake Yeast Containing a Dominant FAS2 Mutation without Extraneous Sequences by a Two-Step Gene Replacement Protocol", Journal of Bioscience and Bioengineering, vol. 87, No. 1, 1999, pp. 43-48, XP55123794A.
Auzat et al., "The NADH oxidase of *Streptococcus pneumoniae*: Its involvement in competence and virulence", Molecular Microbiology, vol. 34, No. 5, 1999, pp. 1018-1028, XP002178490A.
Branden et al., "Introduction to Protein Structure: Prediction, Engineering and Design of Protein Structures", Garland Publishing, Inc., 1991, p. 247.
Chenault et al., "Regeneration of Nicotinamide Cofactors for use in Organic Synthesis", Applied Biochemistry and Biotechnology, vol. 14, 1987, pp. 147-197.
Chica et al., "Semi-rational approaches to engineering enzyme activity: combining the benefits of directed evolution and rational design", Current Opinion in Biotechnology, vol. 16, 2005 (Published online Jul. 1, 2005), pp. 378-384.
Current Protocols in Molecular Biology, Preparations and Analysis of DNA, Supplement 21 (2.10.8) and Supplement 26 (2.10.10) and Hybridization Analysis of DNA Blots Supplement 21 (2.10.9) and Supplement 26 (2.10.11), 4 pages.
Findrik et al., "Coenzyme regeneration catalyzed by NADH oxidase from *Lactobacillus brevis* in the reaction of L-amino acid oxidation", Biochemical Engineering Journal, vol. 39, 2008, pp. 319-327.
GenBank Accession No. AEUW02000001.1, Nov. 18, 2011, 2 pages.
GenBank Accession No. EHJ52306.1, Nov. 18, 2011, 2 pages.
GenBank Accession No. WP_003080172, Aug. 1, 2013, 2 pages.
GENESEQP: AAY95047, Jun. 23, 2000, XP-002561806, 1 page.
Geueke et al., "NADH oxidase from *Lactobacillus brevis*: a new catalyst for the regeneration of NAD", Enzyme and Microbial Technology, vol. 32, 2003, pp. 205-211.
Guo et al., "Protein tolerance to random amino acid change", PNAS, vol. 101, No. 25, Jun. 22, 2004, pp. 9205-9210.
Higuchi et al., Functions of Two Types of NADH Oxidases in Energy Metabolism and Oxidative Stress of *Streptococcus mutans.*, J. Bacteriol., vol. 181, No. 19, Oct. 1999, pp. 5940-5947.
Higuchi et al., "Identification of two distinct NADH oxidases corresponding to $H_2O_2$-forming oxidase and $H_2O$-forming oxidase induced in *Streptococcus mutans*", Journal of General Microbiology, vol. 139, 1993, pp. 2343-2351.
Hummel et al., "An Efficient and Selective Enzymatic Oxidation System for the Synthesis of Enantiomerically Pure D-tert-Leucine", Organic Letters, vol. 5, No. 20, 2003, pp. 3649-3650.
International Preliminary Report on Patentability and Written Opinion of the International Searching Authority (Forms PCT/IB/373 and PCT/ISA/237) and English translation thereof, dated Aug. 7, 2012, for International Application No. PCT/JP2011/050824.
International Preliminary Report on Patentability and English translation of the Written Opinion of the International Searching Authority (Forms PCT/IB/373 and PCT/ISA/237), dated Jun. 3, 2009, for International Application No. PCT/JP2007/072813.
Iwasaki et al., "2P0968B: Synthesis (2) of (S)-3-chloro-1, 2-propanediol by catalytic stereoinversion method", Nippon Nogei Kagakukai Taikai Koen Yoshishu, 2009, p. 121 (1 page), partial English translation.
JPOP: BD675875, Nov. 19, 2003, XP002561807A.
Kroutil et al., "Recent advances in the biocatalytic reduction of ketones and oxidation of sec-alcohols", Current Opinion in Chemical Biology, vol. 8, 2004, pp. 120-126.
Liese et al., "Industrial Biotransformations", The Enzyme Classification, WILEY-VCH, Second, Completely Revised and Extended Edition, 2006, Chapter 2: The Enzyme Classification, pp. 40-42.
Matsumoto et al., "Molecular Cloning and Sequence Analysis of the Gene Encoding the $H_2O$-forming NADH Oxidase from *Streptococcus mutans*", Biosci. Biotech. Biochem., vol. 60, No. 1, 1996, pp. 39-43.
NCBI Reference Sequence: WP_018364669.1, Jun. 28, 2013, 1 page.
Riebel et al., "Cofactor Regeneration of both NAD+ from NADH and NADP+ from NADPH: NADH Oxidase from *Lactobacillus sanfranciscensis*", Adv. Synth. Catal. vol. 345, 2003, pp. 707-712.
Score Search Results Details for Application 12516388: Accession No. AB010636, Jan. 28, 1998. 2 pages.
Score Search Results Details for Application 12516388: Accession No. 042703, Jun. 1, 1998, 2 pages.
Seffernick et al., "Melamine Deaminase and Atrazine Chlorohydrolase: 98 Percent Identical but Functionally Different", Journal of Bacteriology, vol. 183, No. 8, Apr. 2001, pp. 2405-2410.
Sen et al., "Developments in Directed Evolution for Improving Enzyme Functions", Appl. Biochem. Biotechnol., vol. 143, 2007, pp. 212-223.
U.S. Notice of Allowance, dated Aug. 31, 2011, for U.S. Appl. No. 12/516,388.
U.S. Notice of Allowance, dated Jul. 20, 2015, for U.S. Appl. No. 13/574,458.
U.S. Office Action, dated Apr. 12, 2011, for U.S. Appl. No. 12/516,388.
U.S. Office Action, dated Mar. 20, 2015, for U.S. Appl. No. 13/574,458.
U.S. Office Action, dated Oct. 2, 2014, for U.S. Appl. No. 13/574,458.
UNIPROT: Q5A958, Apr. 26, 2005, XP-002561805, 1 page.
Wandrey et al., "Industrial Biocatalysis: Past, Present, and Future", Organic Process Research & Development, vol. 4, No. 4, 2000, pp. 286-290.
Witkowski et al., "Conversion of a β-Ketoacyl Synthase to a Malonyl Decarboxylase by Replacement of the Active-Site Cysteine with Glutamine", Biochemistry, vol. 38, No. 36, 1999, pp. 11643-11650.
Ehsani, Maryam et al., "Reversal of Coenzyme Specificity of 2,3-Butanediol Dehydrogenase . . . " Biotechnology and Bioengineering, 2009, vol. 104, No. 2, pp. 381-389.
Extended European Search Report for European Application No. 12803805.6 dated Apr. 24, 2015.
Gibrat, Jean-Francois et al., "Surprising similarities in structure comparison", Current Opinion in Structural Biology, 1996, vol. 6, No. 3, pp. 377-385.
Nordling, Erik et al., "Medium-chain dehydrogenases/reductases (MDR)", Eur. J. Biochem., 2002, vol. 269, No. 17, pp. 4267-4276.
Watanabe, Seiya et al., "Complete Reversal of Coenzyme Specificity of Xylitol Dehydrogenase . . . ", J. of Biological Chemistry, 2005, vol. 280, No. 11, pp. 10340-10349.
Accession No. F2L599, version 1, UniProt [online] http://www.uniprot.org/uniprot/F2L599, accessed 2016.
Accession No. P42327, version 65, UniProt [online] http://www.uniprot.org/uniprot/P42327, accessed 2016.

* cited by examiner

```
                        SEQUENCE LISTING

<160> NUMBER OF SEQ ID NOS: 31

<210> SEQ ID NO 1
<211> LENGTH: 336
<212> TYPE: PRT
<213> ORGANISM: Candida maltosa

<400> SEQUENCE: 1

Met Ser Ile Pro Ser Thr Gln Tyr Gly Phe Tyr Tyr Thr Lys Glu Lys
1               5                   10                  15

Gly Leu Thr Leu Lys Gln Asp Leu Pro Val Pro Lys Pro Ala Ala Gly
            20                  25                  30

Gln Leu Leu Met Lys Val Asp Ala Val Gly Leu Cys His Ser Asp Leu
        35                  40                  45

His Val Ile Tyr Glu Gly Leu Asp Cys Gly Asp Asn Tyr Val Met Gly
    50                  55                  60

His Glu Ile Ala Gly Thr Val Ala Ala Leu Gly Ala Glu Val Asp Gly
65                  70                  75                  80

Phe Ala Val Gly Asp Arg Val Ala Cys Val Gly Pro Asn Gly Cys Gly
                85                  90                  95

Ile Cys Lys His Cys Leu Lys Gly Glu Asp Asn Val Cys Lys Lys Ala
            100                 105                 110

Phe Gly Asp Trp Phe Gly Leu Gly Ser Asp Gly Gly Tyr Glu Glu Tyr
        115                 120                 125

Leu Leu Val Arg Arg Pro Arg Asn Leu Val Lys Ile Pro Asp Asn Val
    130                 135                 140

Thr Thr Glu Glu Ala Ala Ala Ile Thr Asp Ala Val Leu Thr Pro Tyr
145                 150                 155                 160

His Ala Ile Lys Val Ala Gly Val Gly Pro Thr Thr Asn Leu Leu Ile
                165                 170                 175

Val Gly Ala Gly Gly Leu Gly Gly Asn Ala Ile Gln Val Ala Lys Ala
            180                 185                 190

Phe Gly Ala Thr Val Thr Val Leu Asp Lys Lys Asp Lys Ala Arg Glu
        195                 200                 205

Gln Ala Lys Ser Leu Gly Ala Asp Asn Val Tyr Asp Glu Leu Pro Ser
    210                 215                 220

Ser Val Glu Pro Gly Ser Phe Asp Val Cys Ile Asp Phe Val Ser Val
225                 230                 235                 240

Gln Ala Thr Phe Asp Leu Cys Gln Thr Tyr Cys Glu Pro Lys Gly Thr
```

```
            245                 250                 255
Ile Ile Pro Val Gly Leu Gly Ala Ser Asn Leu Ser Ile Asn Leu Gly
            260                 265                 270

Asp Leu Asp Leu Arg Glu Ile Arg Val Leu Gly Ser Phe Trp Gly Thr
            275                 280                 285

Ser Leu Asp Leu Arg Glu Ala Phe Glu Leu Ala Ala Gln Gly Lys Val
            290                 295                 300

Lys Pro Val Val Ala His Ala Glu Leu Lys Glu Leu Pro Glu Tyr Ile
305                 310                 315                 320

Glu Lys Leu Lys Lys Gly Ala Tyr Gly Arg Val Val Phe His Pro
            325                 330                 335

<210> SEQ ID NO 2
<211> LENGTH: 336
<212> TYPE: PRT
<213> ORGANISM: Artificial Sequence
<220> FEATURE:
<223> OTHER INFORMATION: Synthetic RMA_Mutant

<400> SEQUENCE: 2

Met Ser Ile Pro Ser Thr Gln Tyr Gly Phe Tyr Tyr Thr Lys Glu Lys
1               5                   10                  15

Gly Leu Thr Leu Lys Gln Asp Leu Pro Val Pro Lys Pro Ala Ala Gly
            20                  25                  30

Gln Leu Met Lys Val Asp Ala Val Gly Leu Cys His Ser Asp Leu
            35                  40                  45

His Val Ile Tyr Glu Gly Leu Asp Cys Gly Asp Asn Tyr Val Met Gly
50                  55                  60

His Glu Ile Ala Gly Thr Val Ala Ala Leu Gly Ala Glu Val Asp Gly
65                  70                  75                  80

Phe Ala Val Gly Asp Arg Val Ala Cys Val Gly Pro Asn Gly Cys Gly
                85                  90                  95

Ile Cys Lys His Cys Leu Lys Gly Glu Asp Asn Val Cys Lys Lys Ala
            100                 105                 110

Phe Gly Asp Trp Phe Gly Leu Gly Ser Asp Gly Gly Tyr Glu Glu Tyr
            115                 120                 125

Leu Leu Val Arg Arg Pro Arg Asn Leu Val Lys Ile Pro Asp Asn Val
130                 135                 140

Thr Thr Glu Glu Ala Ala Ile Thr Asp Ala Val Leu Thr Pro Tyr
145                 150                 155                 160

His Ala Ile Lys Val Ala Gly Val Gly Pro Thr Thr Asn Leu Leu Ile
                165                 170                 175

Val Gly Ala Gly Gly Leu Gly Gly Asn Ala Ile Gln Val Ala Lys Ala
            180                 185                 190

Phe Gly Ala Thr Val Thr Val Leu Ser Arg Lys Asp Lys Lys Arg Glu
            195                 200                 205

Gln Ala Lys Ser Leu Gly Ala Asp Asn Val Tyr Asp Glu Leu Pro Ser
        210                 215                 220

Ser Val Glu Pro Gly Ser Phe Asp Val Cys Ile Asp Phe Val Ser Val
225                 230                 235                 240

Gln Ala Thr Phe Asp Leu Cys Gln Thr Tyr Cys Glu Pro Lys Gly Thr
                245                 250                 255

Ile Ile Pro Val Gly Leu Gly Ala Ser Asn Leu Ser Ile Asn Leu Gly
            260                 265                 270

Asp Leu Asp Leu Arg Glu Ile Arg Val Leu Gly Ser Phe Trp Gly Thr
```

```
            275                 280                 285
Ser Leu Asp Leu Arg Glu Ala Phe Glu Leu Ala Ala Gln Gly Lys Val
    290                 295                 300

Lys Pro Val Val Ala His Ala Glu Leu Lys Glu Leu Pro Glu Tyr Ile
305                 310                 315                 320

Glu Lys Leu Lys Lys Gly Ala Tyr Glu Gly Arg Val Val Phe His Pro
                325                 330                 335

<210> SEQ ID NO 3
<211> LENGTH: 336
<212> TYPE: PRT
<213> ORGANISM: Artificial Sequence
<220> FEATURE:
<223> OTHER INFORMATION: Synthetic RMA_Mutant

<400> SEQUENCE: 3

Met Ser Ile Pro Ser Thr Gln Tyr Gly Phe Tyr Tyr Thr Lys Glu Lys
1               5                   10                  15

Gly Leu Thr Leu Lys Gln Asp Leu Pro Val Pro Lys Pro Ala Ala Gly
                20                  25                  30

Gln Leu Leu Met Lys Val Asp Ala Val Gly Leu Cys His Ser Asp Leu
            35                  40                  45

His Val Ile Tyr Glu Gly Leu Asp Cys Gly Asp Asn Tyr Val Met Gly
    50                  55                  60

His Glu Ile Ala Gly Thr Val Ala Ala Leu Gly Ala Glu Val Asp Gly
65                  70                  75                  80

Phe Ala Val Gly Asp Arg Val Ala Cys Val Gly Pro Asn Gly Cys Gly
                85                  90                  95

Ile Cys Lys His Cys Leu Lys Gly Glu Asp Asn Val Cys Lys Lys Ala
            100                 105                 110

Phe Gly Asp Trp Phe Gly Leu Gly Ser Asp Gly Gly Tyr Glu Glu Tyr
        115                 120                 125

Leu Leu Val Arg Arg Pro Arg Asn Leu Val Lys Ile Pro Asp Asn Val
    130                 135                 140

Thr Thr Glu Glu Ala Ala Ala Ile Thr Asp Ala Val Leu Thr Pro Tyr
145                 150                 155                 160

His Ala Ile Lys Val Ala Gly Val Gly Pro Thr Thr Asn Leu Leu Ile
                165                 170                 175

Val Gly Ala Gly Gly Leu Gly Gly Asn Ala Ile Gln Val Ala Lys Ala
            180                 185                 190

Phe Gly Ala Thr Val Thr Val Leu Ala Arg Lys Asp Lys Lys Arg Glu
        195                 200                 205

Gln Ala Lys Ser Leu Gly Ala Asp Asn Val Tyr Asp Glu Leu Pro Ser
    210                 215                 220

Ser Val Glu Pro Gly Ser Phe Asp Val Cys Ile Asp Phe Val Ser Val
225                 230                 235                 240

Gln Ala Thr Phe Asp Leu Cys Gln Thr Tyr Cys Glu Pro Lys Gly Thr
                245                 250                 255

Ile Ile Pro Val Gly Leu Gly Ala Ser Asn Leu Ser Ile Asn Leu Gly
            260                 265                 270

Asp Leu Asp Leu Arg Glu Ile Arg Val Leu Gly Ser Phe Trp Gly Thr
        275                 280                 285

Ser Leu Asp Leu Arg Glu Ala Phe Glu Leu Ala Ala Gln Gly Lys Val
    290                 295                 300

Lys Pro Val Val Ala His Ala Glu Leu Lys Glu Leu Pro Glu Tyr Ile
```

```
                305                 310                 315                 320
Glu Lys Leu Lys Lys Gly Ala Tyr Glu Gly Arg Val Val Phe His Pro
            325                 330                 335

<210> SEQ ID NO 4
<211> LENGTH: 336
<212> TYPE: PRT
<213> ORGANISM: Artificial Sequence
<220> FEATURE:
<223> OTHER INFORMATION: Synthetic RMA_Mutant

<400> SEQUENCE: 4

Met Ser Ile Pro Ser Thr Gln Tyr Gly Phe Tyr Tyr Thr Lys Glu Lys
1               5                   10                  15

Gly Leu Thr Leu Lys Gln Asp Leu Pro Val Pro Lys Pro Ala Ala Gly
            20                  25                  30

Gln Leu Met Lys Val Asp Ala Val Gly Leu Cys His Ser Asp Leu
        35                  40                  45

His Val Ile Tyr Glu Gly Leu Asp Cys Gly Asp Asn Tyr Val Met Gly
    50                  55                  60

His Glu Ile Ala Gly Thr Val Ala Ala Leu Gly Ala Glu Val Asp Gly
65                  70                  75                  80

Phe Ala Val Gly Asp Arg Val Ala Cys Val Gly Pro Asn Gly Cys Gly
                85                  90                  95

Ile Cys Lys His Cys Leu Lys Gly Glu Asp Asn Val Cys Lys Lys Ala
            100                 105                 110

Phe Gly Asp Trp Phe Gly Leu Gly Ser Asp Gly Gly Tyr Glu Glu Tyr
        115                 120                 125

Leu Leu Val Arg Arg Pro Arg Asn Leu Val Lys Ile Pro Asp Asn Val
    130                 135                 140

Thr Thr Glu Glu Ala Ala Ile Thr Asp Ala Val Leu Thr Pro Tyr
145                 150                 155                 160

His Ala Ile Lys Val Ala Gly Val Gly Pro Thr Thr Asn Leu Leu Ile
                165                 170                 175

Val Gly Ala Gly Gly Leu Gly Gly Asn Ala Ile Gln Val Ala Lys Ala
            180                 185                 190

Phe Gly Ala Thr Val Thr Val Leu Ser Arg Ser Asp Lys Lys Arg Glu
        195                 200                 205

Gln Ala Lys Ser Leu Gly Ala Asp Asn Val Tyr Asp Glu Leu Pro Ser
    210                 215                 220

Ser Val Glu Pro Gly Ser Phe Asp Val Cys Ile Asp Phe Val Ser Val
225                 230                 235                 240

Gln Ala Thr Phe Asp Leu Cys Gln Thr Tyr Cys Glu Pro Lys Gly Thr
                245                 250                 255

Ile Ile Pro Val Gly Leu Gly Ala Ser Asn Leu Ser Ile Asn Leu Gly
            260                 265                 270

Asp Leu Asp Leu Arg Glu Ile Arg Val Leu Gly Ser Phe Trp Gly Thr
        275                 280                 285

Ser Leu Asp Leu Arg Glu Ala Phe Glu Leu Ala Ala Gln Gly Lys Val
    290                 295                 300

Lys Pro Val Val Ala His Ala Glu Leu Lys Leu Pro Glu Tyr Ile
305                 310                 315                 320

Glu Lys Leu Lys Lys Gly Ala Tyr Glu Gly Arg Val Val Phe His Pro
                325                 330                 335
```

<210> SEQ ID NO 5
<211> LENGTH: 336
<212> TYPE: PRT
<213> ORGANISM: Artificial Sequence
<220> FEATURE:
<223> OTHER INFORMATION: Synthetic RMA_Mutant

<400> SEQUENCE: 5

```
Met Ser Ile Pro Ser Thr Gln Tyr Gly Phe Tyr Tyr Thr Lys Glu Lys
1               5                   10                  15

Gly Leu Thr Leu Lys Gln Asp Leu Pro Val Pro Lys Pro Ala Ala Gly
            20                  25                  30

Gln Leu Leu Met Lys Val Asp Ala Val Gly Leu Cys His Ser Asp Leu
        35                  40                  45

His Val Ile Tyr Glu Gly Leu Asp Cys Gly Asp Asn Tyr Val Met Gly
    50                  55                  60

His Glu Ile Ala Gly Thr Val Ala Ala Leu Gly Ala Glu Val Asp Gly
65                  70                  75                  80

Phe Ala Val Gly Asp Arg Val Ala Cys Val Gly Pro Asn Gly Cys Gly
                85                  90                  95

Ile Cys Lys His Cys Leu Lys Gly Glu Asp Asn Val Cys Lys Lys Ala
            100                 105                 110

Phe Gly Asp Trp Phe Gly Leu Gly Ser Asp Gly Gly Tyr Glu Glu Tyr
        115                 120                 125

Leu Leu Val Arg Arg Pro Arg Asn Leu Val Lys Ile Pro Asp Asn Val
    130                 135                 140

Thr Thr Glu Glu Ala Ala Ala Ile Thr Asp Ala Val Leu Thr Pro Tyr
145                 150                 155                 160

His Ala Ile Lys Val Ala Gly Val Gly Pro Thr Thr Asn Leu Leu Ile
                165                 170                 175

Val Gly Ala Gly Gly Leu Gly Gly Asn Ala Ile Gln Val Ala Lys Ala
            180                 185                 190

Phe Gly Ala Thr Val Thr Val Leu Ala Arg Ser Asp Lys Lys Arg Glu
        195                 200                 205

Gln Ala Lys Ser Leu Gly Ala Asp Asn Val Tyr Asp Glu Leu Pro Ser
    210                 215                 220

Ser Val Glu Pro Gly Ser Phe Asp Val Cys Ile Asp Phe Val Ser Val
225                 230                 235                 240

Gln Ala Thr Phe Asp Leu Cys Gln Thr Tyr Cys Glu Pro Lys Gly Thr
                245                 250                 255

Ile Ile Pro Val Gly Leu Gly Ala Ser Asn Leu Ser Ile Asn Leu Gly
            260                 265                 270

Asp Leu Asp Leu Arg Glu Ile Arg Val Leu Gly Ser Phe Trp Gly Thr
        275                 280                 285

Ser Leu Asp Leu Arg Glu Ala Phe Glu Leu Ala Ala Gln Gly Lys Val
    290                 295                 300

Lys Pro Val Val Ala His Ala Glu Leu Lys Glu Leu Pro Glu Tyr Ile
305                 310                 315                 320

Glu Lys Leu Lys Lys Gly Ala Tyr Glu Gly Arg Val Val Phe His Pro
                325                 330                 335
```

<210> SEQ ID NO 6
<211> LENGTH: 336
<212> TYPE: PRT
<213> ORGANISM: Artificial Sequence
<220> FEATURE:
<223> OTHER INFORMATION: Synthetic RMA_Mutant

<400> SEQUENCE: 6

```
Met Ser Ile Pro Ser Thr Gln Tyr Gly Phe Tyr Tyr Thr Lys Glu Lys
1               5                   10                  15

Gly Leu Thr Leu Lys Gln Asp Leu Pro Val Pro Lys Pro Ala Ala Gly
            20                  25                  30

Gln Leu Leu Met Lys Val Asp Ala Val Gly Leu Cys His Ser Asp Leu
        35                  40                  45

His Val Ile Tyr Glu Gly Leu Asp Cys Gly Asp Asn Tyr Val Met Gly
    50                  55                  60

His Glu Ile Ala Gly Thr Val Ala Ala Leu Gly Ala Glu Val Asp Gly
65                  70                  75                  80

Phe Ala Val Gly Asp Arg Val Ala Cys Val Gly Pro Asn Gly Cys Gly
                85                  90                  95

Ile Cys Lys His Cys Leu Lys Gly Glu Asp Asn Val Cys Lys Lys Ala
            100                 105                 110

Phe Gly Asp Trp Phe Gly Leu Gly Ser Asp Gly Gly Tyr Glu Glu Tyr
        115                 120                 125

Leu Leu Val Arg Arg Pro Arg Asn Leu Val Lys Ile Pro Asp Asn Val
130                 135                 140

Thr Thr Glu Glu Ala Ala Ile Thr Asp Ala Val Leu Thr Pro Tyr
145                 150                 155                 160

His Ala Ile Lys Val Ala Gly Val Gly Pro Thr Thr Asn Leu Leu Ile
                165                 170                 175

Val Gly Ala Gly Gly Leu Gly Gly Asn Ala Ile Gln Val Ala Lys Ala
            180                 185                 190

Phe Gly Ala Thr Val Thr Val Leu Ser Lys Ser Asp Lys Lys Arg Glu
        195                 200                 205

Gln Ala Lys Ser Leu Gly Ala Asp Asn Val Tyr Asp Glu Leu Pro Ser
    210                 215                 220

Ser Val Glu Pro Gly Ser Phe Asp Val Cys Ile Asp Phe Val Ser Val
225                 230                 235                 240

Gln Ala Thr Phe Asp Leu Cys Gln Thr Tyr Cys Glu Pro Lys Gly Thr
                245                 250                 255

Ile Ile Pro Val Gly Leu Gly Ala Ser Asn Leu Ser Ile Asn Leu Gly
            260                 265                 270

Asp Leu Asp Leu Arg Glu Ile Arg Val Leu Gly Ser Phe Trp Gly Thr
        275                 280                 285

Ser Leu Asp Leu Arg Glu Ala Phe Glu Leu Ala Ala Gln Gly Lys Val
    290                 295                 300

Lys Pro Val Val Ala His Ala Glu Leu Lys Glu Leu Pro Glu Tyr Ile
305                 310                 315                 320

Glu Lys Leu Lys Lys Gly Ala Tyr Glu Gly Arg Val Val Phe His Pro
                325                 330                 335
```

<210> SEQ ID NO 7
<211> LENGTH: 336
<212> TYPE: PRT
<213> ORGANISM: Artificial Sequence
<220> FEATURE:
<223> OTHER INFORMATION: Synthetic RMA_Mutant

<400> SEQUENCE: 7

```
Met Ser Ile Pro Ser Thr Gln Tyr Gly Phe Tyr Tyr Thr Lys Glu Lys
1               5                   10                  15
```

Gly Leu Thr Leu Lys Gln Asp Leu Pro Val Pro Lys Pro Ala Ala Gly
            20                  25                  30

Gln Leu Leu Met Lys Val Asp Ala Val Gly Leu Cys His Ser Asp Leu
        35                  40                  45

His Val Ile Tyr Glu Gly Leu Asp Cys Gly Asp Asn Tyr Val Met Gly
 50                  55                  60

His Glu Ile Ala Gly Thr Val Ala Ala Leu Gly Ala Glu Val Asp Gly
65                  70                  75                  80

Phe Ala Val Gly Asp Arg Val Ala Cys Val Pro Asn Gly Cys Gly
                85                  90                  95

Ile Cys Lys His Cys Leu Lys Gly Glu Asp Asn Val Cys Lys Lys Ala
            100                 105                 110

Phe Gly Asp Trp Phe Gly Leu Gly Ser Asp Gly Gly Tyr Glu Glu Tyr
        115                 120                 125

Leu Leu Val Arg Arg Pro Arg Asn Leu Val Lys Ile Pro Asp Asn Val
130                 135                 140

Thr Thr Glu Glu Ala Ala Ala Ile Thr Asp Ala Val Leu Thr Pro Tyr
145                 150                 155                 160

His Ala Ile Lys Val Ala Gly Val Gly Pro Thr Thr Asn Leu Leu Ile
                165                 170                 175

Val Gly Ala Gly Gly Leu Gly Gly Asn Ala Ile Gln Val Ala Lys Ala
            180                 185                 190

Phe Gly Ala Thr Val Thr Val Leu Ala Lys Ser Asp Lys Lys Arg Glu
        195                 200                 205

Gln Ala Lys Ser Leu Gly Ala Asp Asn Val Tyr Asp Glu Leu Pro Ser
210                 215                 220

Ser Val Glu Pro Gly Ser Phe Asp Val Cys Ile Asp Phe Val Ser Val
225                 230                 235                 240

Gln Ala Thr Phe Asp Leu Cys Gln Thr Tyr Cys Glu Pro Lys Gly Thr
                245                 250                 255

Ile Ile Pro Val Gly Leu Gly Ala Ser Asn Leu Ser Ile Asn Leu Gly
            260                 265                 270

Asp Leu Asp Leu Arg Glu Ile Arg Val Leu Gly Ser Phe Trp Gly Thr
        275                 280                 285

Ser Leu Asp Leu Arg Glu Ala Phe Glu Leu Ala Ala Gln Gly Lys Val
290                 295                 300

Lys Pro Val Val Ala His Ala Glu Leu Lys Glu Leu Pro Glu Tyr Ile
305                 310                 315                 320

Glu Lys Leu Lys Lys Gly Ala Tyr Glu Gly Arg Val Val Phe His Pro
                325                 330                 335

<210> SEQ ID NO 8
<211> LENGTH: 336
<212> TYPE: PRT
<213> ORGANISM: Artificial Sequence
<220> FEATURE:
<223> OTHER INFORMATION: Synthetic RMA_Mutant

<400> SEQUENCE: 8

Met Ser Ile Pro Ser Thr Gln Tyr Gly Phe Tyr Tyr Thr Lys Glu Lys
1               5                   10                  15

Gly Leu Thr Leu Lys Gln Asp Leu Pro Val Pro Lys Pro Ala Ala Gly
            20                  25                  30

Gln Leu Leu Met Lys Val Asp Ala Val Gly Leu Cys His Ser Asp Leu
        35                  40                  45

His Val Ile Tyr Glu Gly Leu Asp Cys Gly Asp Asn Tyr Val Met Gly
 50                  55                  60

His Glu Ile Ala Gly Thr Val Ala Ala Leu Gly Ala Glu Val Asp Gly
 65                  70                  75                  80

Phe Ala Val Gly Asp Arg Val Ala Cys Val Gly Pro Asn Gly Cys Gly
                 85                  90                  95

Ile Cys Lys His Cys Leu Lys Gly Glu Asp Asn Val Cys Lys Lys Ala
            100                 105                 110

Phe Gly Asp Trp Phe Gly Leu Gly Ser Asp Gly Gly Tyr Glu Glu Tyr
            115                 120                 125

Leu Leu Val Arg Arg Pro Arg Asn Leu Val Lys Ile Pro Asp Asn Val
130                 135                 140

Thr Thr Glu Glu Ala Ala Ala Ile Thr Asp Ala Val Leu Thr Pro Tyr
145                 150                 155                 160

His Ala Ile Lys Val Ala Gly Val Gly Pro Thr Thr Asn Leu Leu Ile
                165                 170                 175

Val Gly Ala Gly Gly Leu Gly Gly Asn Ala Ile Gln Val Ala Lys Ala
            180                 185                 190

Phe Gly Ala Thr Val Thr Val Leu Ser Arg Lys Asp Lys Ala Arg Glu
            195                 200                 205

Gln Ala Lys Ser Leu Gly Ala Asp Asn Val Tyr Asp Glu Leu Pro Ser
210                 215                 220

Ser Val Glu Pro Gly Ser Phe Asp Val Cys Ile Asp Phe Val Ser Val
225                 230                 235                 240

Gln Ala Thr Phe Asp Leu Cys Gln Thr Tyr Cys Glu Pro Lys Gly Thr
                245                 250                 255

Ile Ile Pro Val Gly Leu Gly Ala Ser Asn Leu Ser Ile Asn Leu Gly
            260                 265                 270

Asp Leu Asp Leu Arg Glu Ile Arg Val Leu Gly Ser Phe Trp Gly Thr
            275                 280                 285

Ser Leu Asp Leu Arg Glu Ala Phe Glu Leu Ala Ala Gln Gly Lys Val
290                 295                 300

Lys Pro Val Val Ala His Ala Glu Leu Lys Glu Leu Pro Glu Tyr Ile
305                 310                 315                 320

Glu Lys Leu Lys Lys Gly Ala Tyr Glu Gly Arg Val Val Phe His Pro
                325                 330                 335

<210> SEQ ID NO 9
<211> LENGTH: 1011
<212> TYPE: DNA
<213> ORGANISM: Artificial Sequence
<220> FEATURE:
<223> OTHER INFORMATION: Synthetic RMA_Code-DNA

<400> SEQUENCE: 9
atgtcaattc catctactca atacggtttc tattacacta agaaaaagg tttaaccttg      60 aaacaagatt tacctgttcc taaaccagct gctggtcaat gttgatgaa ggtcgatgcc     120 gttggtttat gtcactctga tttacatgtc atttatgaag ggttagattg tggggataac    180
tatgtcatgg acatgaaat tgccggtact gttgctgctt gggtgctga agttgacggt      240 tttgctgttg gtgatcgtgt tgcttgtgtt ggtccaaatg gttgtggtat ctgtaaacat    300
tgtttgaaag gtgaagataa cgtttgtaag aaggcttttg gtgattggtt tggtttaggt    360
agtgatggtg gttatgaaga atacttgttg gttagaagac caagaaattt ggttaaaatc    420
ccagataatg tcactactga agaagctgcc gctattactg atgctgtttt gactccttac    480

```
catgctatta aggttgctgg tgttggtcca actactaatc ttttaattgt tggtgctggt      540
ggtttgggtg gtaatgctat ccaagttgcc aaagcttttg gtgctacagt tactgttttg      600
gataagaaag ataaggctcg tgaacaagct aagagtttgg gtgctgataa tgtttatgat      660
gaattaccat caagtgtcga accaggttct tttgatgtat gtattgattt tgtgtctgtt      720
caagcaactt ttgacctttg tcaaacatat tgtgaaccaa aaggtaccat cattccagtt      780
ggtttaggtg cttcaaatct ttccatcaac cttggtgatt tagatcttcg tgaaatcaga      840
gttttgggta gtttctgggg tacctctttg gacttgagag aagcttttga attggccgct      900
caaggtaaag tcaaaccagt tgttgcccat gctgaattga agaattacc agaatacatt       960 gaaaaattga agaaggtgc ttatgaaggt agagttgttt tccatccata a                1011

<210> SEQ ID NO 10
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 10
gataagaaag ataagaaacg tgaacaagct aag                                   33

<210> SEQ ID NO 11
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 11
cttagcttgt tcacgtttct tatctttctt atc                                   33

<210> SEQ ID NO 12
<211> LENGTH: 1011
<212> TYPE: DNA
<213> ORGANISM: Artificial Sequence
<220> FEATURE:
<223> OTHER INFORMATION: Synthetic RMA_Code-DNA

<400> SEQUENCE: 12
atgtcaattc catctactca atacggtttc tattacacta agaaaaagg tttaaccttg        60 aaacaagatt tacctgttcc taaaccagct gctggtcaat tgttgatgaa ggtcgatgcc      120
gttggtttat gtcactctga tttacatgtc atttatgaag ggttagattg tggggataac      180
tatgtcatgg gacatgaaat tgccggtact gttgctgctt ggggtgctga agttgacggt      240
tttgctgttg gtgatcgtgt tgcttgtgtt ggtccaaatg gttgtggtat ctgtaaacat      300
tgtttgaaag gtgaagataa cgtttgtaag aaggcttttg gtgattggtt tggtttaggt      360
agtgatggtg gttatgaaga atacttgttg gttagaagac caagaaattt ggttaaaatc      420
ccagataatg tcactactga agaagctgcc gctattactg atgctgtttt gactcccttac     480 catgctatta aggttgctgg tgttggtcca actactaatc ttttaattgt tggtgctggt      540
ggtttgggtg gtaatgctat ccaagttgcc aaagcttttg gtgctacagt tactgttttg      600
gataagaaag ataagaaacg tgaacaagct aagagtttgg gtgctgataa tgtttatgat      660
gaattaccat caagtgtcga accaggttct tttgatgtat gtattgattt tgtgtctgtt      720
caagcaactt ttgacctttg tcaaacatat tgtgaaccaa aaggtaccat cattccagtt      780
```

```
ggtttaggtg cttcaaatct ttccatcaac cttggtgatt tagatcttcg tgaaatcaga      840
gttttgggta gtttctgggg tacctctttg gacttgagag aagcttttga attggccgct      900
caaggtaaag tcaaaccagt tgttgcccat gctgaattga agaattacc  agaatacatt      960 gaaaaattga agaaggtgc  ttatgaaggt agagttgttt tccatccata a              1011
```

```
<210> SEQ ID NO 13
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 13
ctgttttgtc taggaaagat aag                                              23

<210> SEQ ID NO 14
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 14
cttatctttc ctagacaaaa cag                                              23

<210> SEQ ID NO 15
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 15
ctgttttggc taggaaagat aag                                              23

<210> SEQ ID NO 16
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 16
cttatctttc ctagccaaaa cag                                              23

<210> SEQ ID NO 17
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 17
ctgttttgtc taggtcagat aag                                              23

<210> SEQ ID NO 18
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 18
cttatctgac ctagacaaaa cag                                              23
```

<210> SEQ ID NO 19
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 19
ctgttttggc taggtcagat aag                                               23

<210> SEQ ID NO 20
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 20
cttatctgac ctagccaaaa cag                                               23

<210> SEQ ID NO 21
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 21
ctgttttgtc taagtcagat aag                                               23

<210> SEQ ID NO 22
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 22
cttatctgac ttagacaaaa cag                                               23

<210> SEQ ID NO 23
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 23
ctgttttggc taagtcagat aag                                               23

<210> SEQ ID NO 24
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 24
cttatctgac ttagccaaaa cag                                               23

<210> SEQ ID NO 25
<211> LENGTH: 1011
<212> TYPE: DNA
<213> ORGANISM: Artificial Sequence
<220> FEATURE:

<223> OTHER INFORMATION: Synthetic RMA_Code-DNA

<400> SEQUENCE: 25

```
atgtcaattc catctactca atacggtttc tattacacta agaaaaagg tttaaccttg      60
aaacaagatt tacctgttcc taaaccagct gctggtcaat tgttgatgaa ggtcgatgcc    120
gttggtttat gtcactctga tttacatgtc atttatgaag ggttagattg tggggataac    180
tatgtcatgg gacatgaaat tgccggtact gttgctgctt gggtgctga agttgacggt    240
tttgctgttg gtgatcgtgt tgcttgtgtt ggtccaaatg gttgtggtat ctgtaaacat    300
tgtttgaaag gtgaagataa cgtttgtaag aaggcttttg gtgattggtt tggtttaggt    360
agtgatggtg gttatgaaga atacttgttg gttagaagac caagaaattt ggttaaaatc    420
ccagataatg tcactactga agaagctgcc gctattactg atgctgtttt gactccttac    480
catgctatta aggttgctgg tgttggtcca actactaatc ttttaattgt tggtgctggt    540
ggtttgggtg gtaatgctat ccaagttgcc aaagcttttg gtgctacagt tactgttttg    600
tctaggaaag ataagaaacg tgaacaagct aagagtttgg gtgctgataa tgtttatgat    660
gaattaccat caagtgtcga accaggttct tttgatgtat gtattgattt tgtgtctgtt    720
caagcaactt ttgacctttg tcaaacatat tgtgaaccaa aaggtaccat cattccagtt    780
ggtttaggtg cttcaaatct ttccatcaac cttggtgatt tagatcttcg tgaaatcaga    840
gttttgggta gtttctgggg tacctctttg gacttgagag aagcttttga attggccgct    900
caaggtaaag tcaaaccagt tgttgcccat gctgaattga agaattacc agaatacatt    960
gaaaaattga agaaggtgc ttatgaaggt agagttgttt ccatccata a              1011
```

<210> SEQ ID NO 26
<211> LENGTH: 1011
<212> TYPE: DNA
<213> ORGANISM: Artificial Sequence
<220> FEATURE:
<223> OTHER INFORMATION: Synthetic RMA_Code-DNA

<400> SEQUENCE: 26

```
atgtcaattc catctactca atacggtttc tattacacta agaaaaagg tttaaccttg      60
aaacaagatt tacctgttcc taaaccagct gctggtcaat tgttgatgaa ggtcgatgcc    120
gttggtttat gtcactctga tttacatgtc atttatgaag ggttagattg tggggataac    180
tatgtcatgg gacatgaaat tgccggtact gttgctgctt gggtgctga agttgacggt    240
tttgctgttg gtgatcgtgt tgcttgtgtt ggtccaaatg gttgtggtat ctgtaaacat    300
tgtttgaaag gtgaagataa cgtttgtaag aaggcttttg gtgattggtt tggtttaggt    360
agtgatggtg gttatgaaga atacttgttg gttagaagac caagaaattt ggttaaaatc    420
ccagataatg tcactactga agaagctgcc gctattactg atgctgtttt gactccttac    480
catgctatta aggttgctgg tgttggtcca actactaatc ttttaattgt tggtgctggt    540
ggtttgggtg gtaatgctat ccaagttgcc aaagcttttg gtgctacagt tactgttttg    600
gctaggaaag ataagaaacg tgaacaagct aagagtttgg gtgctgataa tgtttatgat    660
gaattaccat caagtgtcga accaggttct tttgatgtat gtattgattt tgtgtctgtt    720
caagcaactt ttgacctttg tcaaacatat tgtgaaccaa aaggtaccat cattccagtt    780
ggtttaggtg cttcaaatct ttccatcaac cttggtgatt tagatcttcg tgaaatcaga    840
gttttgggta gtttctgggg tacctctttg gacttgagag aagcttttga attggccgct    900
caaggtaaag tcaaaccagt tgttgcccat gctgaattga agaattacc agaatacatt    960
```
gaaaaattga agaaaggtgc ttatgaaggt agagttgttt tccatccata a          1011

```
<210> SEQ ID NO 27
<211> LENGTH: 1011
<212> TYPE: DNA
<213> ORGANISM: Artificial Sequence
<220> FEATURE:
<223> OTHER INFORMATION: Synthetic RMA_Code-DNA

<400> SEQUENCE: 27
```
atgtcaattc catctactca atacggtttc tattacacta agaaaaagg tttaaccttg    60 aaacaagatt tacctgttcc taaaccagct gctggtcaat tgttgatgaa ggtcgatgcc   120
gttggtttat gtcactctga tttacatgtc atttatgaag ggttagattg tggggataac   180
tatgtcatgg gacatgaaat tgccggtact gttgctgctt tgggtgctga agttgacggt   240
tttgctgttg gtgatcgtgt tgcttgtgtt ggtccaaatg gttgtggtat ctgtaaacat   300
tgtttgaaag gtgaagataa cgtttgtaag aaggcttttg gtgattggtt tggtttaggt   360
agtgatggtg gttatgaaga atacttgttg gttagaagac caagaaattt ggttaaaatc   420
ccagataatg tcactactga agaagctgcc gctattactg atgctgtttt gactccttac   480
catgctatta aggttgctgg tgttggtcca actactaatc tttttaattgt tggtgctggt   540 ggtttgggtg gtaatgctat ccaagttgcc aaagcttttg gtgctacagt tactgttttg   600
tctaggtcag ataagaaacg tgaacaagct aagagtttgg gtgctgataa tgtttatgat   660
gaattaccat caagtgtcga accaggttct tttgatgtat gtattgattt tgtgtctgtt   720
caagcaactt ttgacctttg tcaaacatat tgtgaaccaa aaggtaccat cattccagtt   780
ggtttaggtg cttcaaatct ttccatcaac cttggtgatt tagatcttcg tgaaatcaga   840
gttttgggta gtttctgggg tacctctttg gacttgagag aagcttttga attggccgct   900
caaggtaaag tcaaaccagt tgttgcccat gctgaattga agaattacc agaatacatt   960 gaaaaattga agaaaggtgc ttatgaaggt agagttgttt tccatccata a          1011

```
<210> SEQ ID NO 28
<211> LENGTH: 1011
<212> TYPE: DNA
<213> ORGANISM: Artificial Sequence
<220> FEATURE:
<223> OTHER INFORMATION: Synthetic RMA_Code-DNA

<400> SEQUENCE: 28
```
atgtcaattc catctactca atacggtttc tattacacta agaaaaagg tttaaccttg    60 aaacaagatt tacctgttcc taaaccagct gctggtcaat tgttgatgaa ggtcgatgcc   120
gttggtttat gtcactctga tttacatgtc atttatgaag ggttagattg tggggataac   180
tatgtcatgg gacatgaaat tgccggtact gttgctgctt tgggtgctga agttgacggt   240
tttgctgttg gtgatcgtgt tgcttgtgtt ggtccaaatg gttgtggtat ctgtaaacat   300
tgtttgaaag gtgaagataa cgtttgtaag aaggcttttg gtgattggtt tggtttaggt   360
agtgatggtg gttatgaaga atacttgttg gttagaagac caagaaattt ggttaaaatc   420
ccagataatg tcactactga agaagctgcc gctattactg atgctgtttt gactccttac   480
catgctatta aggttgctgg tgttggtcca actactaatc tttttaattgt tggtgctggt   540 ggtttgggtg gtaatgctat ccaagttgcc aaagcttttg gtgctacagt tactgttttg   600
gctaggtcag ataagaaacg tgaacaagct aagagtttgg gtgctgataa tgtttatgat   660

```
gaattaccat caagtgtcga accaggttct tttgatgtat gtattgattt tgtgtctgtt      720
caagcaactt ttgacctttg tcaaacatat tgtgaaccaa aaggtaccat cattccagtt      780
ggtttaggtg cttcaaatct ttccatcaac cttggtgatt tagatcttcg tgaaatcaga      840
gttttgggta gtttctgggg tacctctttg gacttgagag aagcttttga attggccgct      900
caaggtaaag tcaaaccagt tgttgcccat gctgaattga aagaattacc agaatacatt      960
gaaaaattga gaaaggtgc ttatgaaggt agagttgttt ccatccata a                1011
```

\<210\> SEQ ID NO 29  
\<211\> LENGTH: 1011  
\<212\> TYPE: DNA  
\<213\> ORGANISM: Artificial Sequence  
\<220\> FEATURE:  
\<223\> OTHER INFORMATION: Synthetic RMA_Code-DNA

\<400\> SEQUENCE: 29

```
atgtcaattc catctactca atacggtttc tattcactca aagaaaaagg tttaaccttg       60
aaacaagatt tacctgttcc taaaccagct gctggtcaat tgttgatgaa ggtcgatgcc      120
gttggtttat gtcactctga tttacatgtc atttatgaag gttagattg tggggataac      180 tatgtcatgg gacatgaaat tgccggtact gttgctgctt gggtgctga agttgacggt      240 tttgctgttg gtgatcgtgt tgcttgtgtt ggtccaaatg gttgtggtat ctgtaaacat      300
tgtttgaaag gtgaagataa cgtttgtaag aaggcttttg gtgattggtt tggtttaggt      360
agtgatggtg gttatgaaga atacttgttg gttagaagac caagaaattt ggttaaaatc      420
ccagataatg tcactactga agaagctgcc gctattactg atgctgtttt gactccttac      480
catgctatta aggttgctgg tgttggtcca actactaatc ttttaattgt tggtgctggt      540
ggtttgggtg gtaatgctat ccaagttgcc aaagcttttg gtgctacagt tactgttttg      600
tctaagtcag ataagaaacg tgaacaagct aagagtttgg gtgctgataa tgtttatgat      660
gaattaccat caagtgtcga accaggttct tttgatgtat gtattgattt tgtgtctgtt      720
caagcaactt ttgacctttg tcaaacatat tgtgaaccaa aaggtaccat cattccagtt      780
ggtttaggtg cttcaaatct ttccatcaac cttggtgatt tagatcttcg tgaaatcaga      840
gttttgggta gtttctgggg tacctctttg gacttgagag aagcttttga attggccgct      900
caaggtaaag tcaaaccagt tgttgcccat gctgaattga aagaattacc agaatacatt      960
gaaaaattga gaaaggtgc ttatgaaggt agagttgttt ccatccata a                1011
```

\<210\> SEQ ID NO 30  
\<211\> LENGTH: 1011  
\<212\> TYPE: DNA  
\<213\> ORGANISM: Artificial Sequence  
\<220\> FEATURE:  
\<223\> OTHER INFORMATION: Synthetic RMA_Code-DNA

\<400\> SEQUENCE: 30

```
atgtcaattc catctactca atacggtttc tattcactca aagaaaaagg tttaaccttg       60
aaacaagatt tacctgttcc taaaccagct gctggtcaat tgttgatgaa ggtcgatgcc      120
gttggtttat gtcactctga tttacatgtc atttatgaag gttagattg tggggataac      180 tatgtcatgg gacatgaaat tgccggtact gttgctgctt gggtgctga agttgacggt      240 tttgctgttg gtgatcgtgt tgcttgtgtt ggtccaaatg gttgtggtat ctgtaaacat      300
tgtttgaaag gtgaagataa cgtttgtaag aaggcttttg gtgattggtt tggtttaggt      360
agtgatggtg gttatgaaga atacttgttg gttagaagac caagaaattt ggttaaaatc      420
```

-continued

```
ccagataatg tcactactga agaagctgcc gctattactg atgctgtttt gactccttac      480
catgctatta aggttgctgg tgttggtcca actactaatc ttttaattgt tggtgctggt      540
ggtttgggtg gtaatgctat ccaagttgcc aaagcttttg gtgctacagt tactgttttg      600
gctaagtcag ataagaaacg tgaacaagct aagagtttgg gtgctgataa tgtttatgat      660
gaattaccat caagtgtcga accaggttct tttgatgtat gtattgattt tgtgtctgtt      720
caagcaactt ttgacctttg tcaaacatat tgtgaaccaa aaggtaccat cattccagtt      780
ggtttaggtg cttcaaatct ttccatcaac cttggtgatt tagatcttcg tgaaatcaga      840
gttttgggta gtttctgggg tacctctttg gacttgagag aagcttttga attggccgct      900
caaggtaaag tcaaaccagt tgttgcccat gctgaattga agaattacc agaatacatt      960 gaaaaattga agaaaggtgc ttatgaaggt agagttgttt ccatccata a              1011

<210> SEQ ID NO 31
<211> LENGTH: 1011
<212> TYPE: DNA
<213> ORGANISM: Artificial Sequence
<220> FEATURE:
<223> OTHER INFORMATION: Synthetic RMA_Code-DNA

<400> SEQUENCE: 31
atgtcaattc catctactca atacggtttc tattacacta agaaaaagg tttaaccttg       60 aaacaagatt tacctgttcc taaaccagct gctggtcaat tgttgatgaa ggtcgatgcc     120
gttggtttat gtcactctga tttacatgtc atttatgaag ggttagattg tggggataac     180
tatgtcatgg gacatgaaat tgccggtact gttgctgctt tgggtgctga agttgacggt     240
tttgctgttg gtgatcgtgt tgcttgtgtt ggtccaaatg gttgtggtat ctgtaaacat     300
tgtttgaaag gtgaagataa cgtttgtaag aaggcttttg gtgattggtt tggtttaggt     360
agtgatggtg gttatgaaga atacttgttg gttagaagac caagaaattt ggttaaaatc     420
ccagataatg tcactactga agaagctgcc gctattactg atgctgtttt gactccttac     480
catgctatta aggttgctgg tgttggtcca actactaatc ttttaattgt tggtgctggt     540
ggtttgggtg gtaatgctat ccaagttgcc aaagcttttg gtgctacagt tactgttttg     600
tctaggaaag ataaggctcg tgaacaagct aagagtttgg gtgctgataa tgtttatgat     660
gaattaccat caagtgtcga accaggttct tttgatgtat gtattgattt tgtgtctgtt     720
caagcaactt ttgacctttg tcaaacatat tgtgaaccaa aaggtaccat cattccagtt     780
ggtttaggtg cttcaaatct ttccatcaac cttggtgatt tagatcttcg tgaaatcaga     840
gttttgggta gtttctgggg tacctctttg gacttgagag aagcttttga attggccgct     900
caaggtaaag tcaaaccagt tgttgcccat gctgaattga agaattacc agaatacatt     960 gaaaaattga agaaaggtgc ttatgaaggt agagttgttt ccatccata a              1011
```

ENZYME FUNCTION MODIFICATION METHOD AND ENZYME VARIANT THEREOF

TECHNICAL FIELD

The present invention relates to a method for altering the coenzyme dependency of alcohol dehydrogenases, in particular, a method for altering the coenzyme dependency of medium-chain dehydrogenases/reductases (MDRs).

BACKGROUND ART

General processes for producing optically active alcohols with oxidoreductases require coenzymes. In order to avoid complete consumption of the coenzymes in these reactions, efficient regeneration of the coenzymes during the reduction/oxidation reactions is important. Examples of coenzymes required for the production of optically active alcohols include pyridine nucleotide coenzymes such as reduced β-nicotinamide adenine dinucleotide phosphate (NADPH, NADP+ for its oxidized form) and reduced β-nicotinamide adenine dinucleotide (NADH, NAD+ for its oxidized form). One known strategy to regenerate these coenzymes is to use glucose dehydrogenase (GDH), formate dehydrogenase (FDH), or the like.

Although alcohol dehydrogenases with good properties (stability, solvent resistance, oxidation resistance) and specific activity have been known, their coenzyme dependency has not been optimized yet. Therefore, their productivity of optically active alcohols is limited even when NADPH or NADH is regenerated. Development of techniques to optimize the coenzyme dependency of alcohol dehydrogenase according to the coenzyme dependency of a coenzyme regeneration enzyme, that is, to optimize alcohol dehydrogenase to be NADPH- or NADH-dependent, will realize easier optimization of production processes of optically active alcohols and more efficient production of optically active alcohols.

Variant screening to identify an enzyme with altered coenzyme dependency takes a lot of effort. Instead, rational designing has been attempted to design a desired enzyme variant with altered coenzyme dependency based on three-dimensional structure data of the enzyme (Patent Literature 1 and Non Patent Literature 1).

Alcohol dehydrogenases (ADH) are a representative group of enzymes including members whose variants with altered coenzyme dependency are known to be obtainable by rational designing. In particular, recent studies have reported success in altering the coenzyme dependency of the short-chain dehydrogenase/reductase (SDR) family, which has about 250 amino acid residues (Non Patent Literature 2, Non Patent Literature 3). Yet, there is no report of success on the medium-chain dehydrogenase/reductase (MDR) family, which has about 350 amino acid residues.

CITATION LIST

Patent Literature

Patent Literature 1: WO 03/004653

Non Patent Literature

Non Patent Literature 1: Penning T. M. et al., "Chem. Rev.", 2001, vol. 101, pp. 3027-3046
Non Patent Literature 2: Machielsen R. et al., "Eng. Life Sci.", 2008, vol. 9, pp. 38-44
Non Patent Literature 3: Zhang R. et al., "Appl. Environ. Microbiol." 2009, pp. 2176-2183

SUMMARY OF INVENTION

Technical Problem

One goal of the present invention is to optimize alcohol dehydrogenases with respect to NADPH or NADH dependency to increase the yield of production of optically active alcohols with the alcohol dehydrogenases coupled to a coenzyme regeneration system.

However, it has been impossible to apply the rational designing techniques for enzymes of different types and different sequence identities to MDRs. Additionally, enzymes of the MDR (medium-chain dehydrogenase/reductase) family containing about 350 amino acid residues, among other alcohol dehydrogenases, contain 350 candidate sites for each single mutation. For multiple-site mutations, they contain countless candidate sites. Moreover, the number of candidate amino acids for substitution in each site is at least 19. Accordingly, it has been extremely difficult to identify a desired variant with altered coenzyme dependency among countless candidates.

Solution to Problem

The present inventors have made intensive studies to solve the above problem, and successfully developed an enzyme alteration method for altering the coenzyme dependency of enzymes of the MDR (medium-chain dehydrogenase/reductase) family. Specifically, the present inventors successfully reduced the number of candidate mutation sites from as many as 350 to only 4, and determined appropriate amino acids for substitution from 19 natural amino acids. This method makes it possible to obtain NADPH/NADP+-dependent enzyme variants from NADH/NAD+-dependent enzymes of the MDR (medium-chain dehydrogenase/reductase) family, and to obtain NADH/NAD+-dependent enzyme variants from NADPH/NADP+-dependent enzymes of the MDR (medium-chain dehydrogenase/reductase) family.

Specifically, the present invention relates to

[1] a protein of medium-chain oxidoreductase family, containing at least one of the following amino acid residues (a) to (d):
(a) Ala or Ser at a position conformationally equivalent to Asp-201 of SEQ ID NO:1;
(b) Arg at a position conformationally equivalent to Lys-202 of SEQ ID NO:1;
(c) Ser at a position conformationally equivalent to Lys-203 of SEQ ID NO:1; and
(d) Lys at a position conformationally equivalent to Ala-206 of SEQ ID NO:1,
[2] the protein of [1], which contains an amino acid sequence having at least 85% sequence identity to the amino acid sequence of SEQ ID NO:1,
[3] the protein of [1] or [2], which contains an amino acid sequence obtained by introducing at least one of the following mutations (e) to (h) into the amino acid sequence of SEQ ID NO:1:
(e) a substitution of Ala or Ser for Asp-201;
(f) a substitution of Arg for Lys-202;
(g) a substitution of Ser for Lys-203; and
(h) a substitution of Lys for Ala-206,
[4] the protein of any one of [1] to [3], which contains any one of the amino acid sequences of SEQ ID NOs:2 to 8,

[5] a DNA, containing a base sequence encoding the protein of any one of [1] to [4],
[6] a DNA, selected from the group consisting of:
(A) DNAs containing any one of the base sequences of SEQ ID NOs:25 to 31;
(B) DNAs which are capable of hybridizing with a DNA containing a base sequence complementary to any one of the base sequences of SEQ ID NOs:25 to 31 under stringent conditions, and contain a base sequence encoding a protein having oxidoreductase activity; and
(C) DNAs having at least 85% sequence identity to any one of the base sequences of SEQ ID NOs:25 to 31, and containing a base sequence encoding a protein having oxidoreductase activity,
[7] a vector, containing the DNA of [6],
[8] a transformant, obtained by transformation of a host cell with the vector of [7],
[9] a culture of the transformant of [8],
[10] a method for producing oxidized nicotinamide adenine dinucleotide phosphate, which includes converting reduced nicotinamide adenine dinucleotide phosphate into oxidized nicotinamide adenine dinucleotide phosphate using the protein of any one of [1] to [5],
[11] a method for producing reduced nicotinamide adenine dinucleotide phosphate, which includes converting oxidized nicotinamide adenine dinucleotide phosphate into reduced nicotinamide adenine dinucleotide phosphate using the protein of [1] or [2],
[12] a method for producing reduced nicotinamide adenine dinucleotide phosphate, which includes allowing a reductase to act on the oxidized nicotinamide adenine dinucleotide phosphate obtained by the method of [10],
[13] a method for producing oxidized nicotinamide adenine dinucleotide phosphate, which includes allowing an oxidase to act on the reduced nicotinamide adenine dinucleotide phosphate obtained by the method of [11],
[14] the production method of any one of [10] to [13], which includes using the transformant of [8] or the culture of [9], and
[15] a compound, obtained by the production method of any one of [10] to [14].

Advantageous Effects of Invention

The present invention makes it possible to optimize the coenzyme dependency of alcohol dehydrogenases (ADHs), in particular, of ADHs of the medium-chain dehydrogenase/reductase (MDR) family, and therefore to increase the yield of production of optically active alcohols with the alcohol dehydrogenases coupled to a coenzyme regeneration system.

A recent finding has revealed that a *Lactobacillus*-derived GDH is a NADP+ reductase having good properties (WO 09/041,415). Unfortunately, this *Lactobacillus*-derived GDH cannot be easily used as a coenzyme regeneration enzyme for RMA, which is a *Candida maltosa*-derived enzyme of the MDR family enzyme. This is because the wild-type RMA is NADH-dependent while the GDH is a NADP+ reductase. By contrast, proteins of the present invention whose coenzyme dependency is altered can be used with the *Lactobacillus*-derived NADP+ reductase GDH. This provides a significant benefit for designing production processes.

Additionally, the techniques of the present invention provide a significant benefit for designing optimal reaction processes of multiple-stage reactions in which a reaction using an NADPH/NADP+-dependent enzyme and a reaction using an NADH/NAD+-dependent enzyme are performed in a single reaction solution because the techniques can alter the coenzyme dependency.

DESCRIPTION OF EMBODIMENTS

Figure 1:
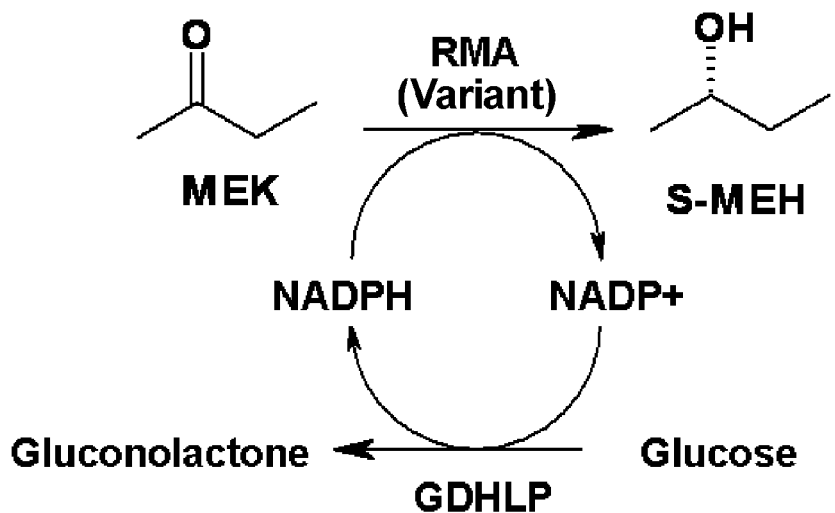
FIG. 1 is a schematic view of reactions in Example 4 of the present invention.

The term "protein" as used herein is intended to include any molecules of polypeptide structure and therefore fragmentized polypeptide chains and polypeptide chains connected by a peptide bond are also included within the scope of this term.

Proteins of the present invention are obtainable by introducing amino acid substitution(s) into proteins of the medium-chain dehydrogenase/reductase family. The medium-chain dehydrogenase/reductase (MDR) family is one of the families of alcohol dehydrogenases (ADHs, EC1.1.1.1.). MDR family enzymes have 350 to 375 residues and most of them contain zinc (Zn). The medium-chain dehydrogenase/reductase family is registered, classified, and defined in various bioinformatics databases. For example, all enzymes relating to the family ID "PF00107" in the Pfam database (http://pfam.sanger.ac.uk/) are classified to the medium-chain dehydrogenase/reductase family, and the number of registered sequences is more than 20,000 as of April 2011. Enzymes of the medium-chain dehydrogenase/reductase family are involved in a wide range of physiological functions including alcohol fermentation, aldehyde detoxification, biosynthesis of lignin, biosynthesis of fatty acids, and protection from oxidative damage.

The proteins of the medium-chain dehydrogenase/reductase family require a pyridine nucleotide as a coenzyme. The term "pyridine nucleotide" refers to β-nicotinamide adenine dinucleotide phosphate (NADPH for its reduced form, NADP+ for its oxidized form) or β-nicotinamide adenine dinucleotide (NADH for its reduced form, NAD+ for oxidized form).

Newly discovered, unregistered sequences are also classified to the medium-chain dehydrogenase/reductase family if they have high sequence identity to an enzyme of the medium-chain dehydrogenase/reductase family. The "sequence identity" can be determined by an amino acid sequence identity analysis using a BLAST program. Preferably, the sequence identity evaluation by the BLAST analysis depends on statistic values called E-values. An E-value closer to 0 corresponds to higher identity. When a judgment is made to determine whether an enzyme is a member of the MDR family based on the sequence identity, the standard E-value to a known enzyme of the MDR family is preferably not more than $1\times10^{-5}$, more preferably not more than $1\times10^{-10}$, and still more preferably not more than $1\times10^{-15}$. Software for the BLAST analysis is available from National Center for Biotechnology Information (http://www.ncbi.nlm.nih.gov/).

The enzymes into which the amino acid residue substitution(s) are to be introduced are preferably selected from enzymes of the medium-chain dehydrogenase/reductase family in the protein sequence database UniProtKB (http://www.uniprot.org/). The technique for converting enzymes to be NADPH/NADP+-dependent can be applied to, for example, the following NADH/NAD+-dependent enzymes of the medium-chain dehydrogenase/reductase family: yeast-derived ADH1 (P00330); *Bacillus*-derived ADH-HT (P42328); and human-derived ADH1β (P00325). Likewise, the technique for converting enzymes to be NADH/NAD+-dependent can be applied to, for example, the following NADPH/NADP+-dependent enzymes of the MDR family: yeast-derived ADH6 (Q04894), *Populus tremuloides*-derived sinapyl ADH (Q94G59), and human-derived PIG3 (Q53FA7). The numbers in the parentheses are their code numbers in the database.

The original unmutated proteins are preferably proteins containing an amino acid sequence with high sequence identity to the *Candida maltosa*-derived enzyme of the MDR family (WO 08/066,018, abbreviated as RMA hereinbelow). The term "sequence identity" refers to the percentage of amino acid residues in a homologous region which match perfectly a reference. The sequence identity is determined by the above-mentioned BLAST analysis, and returned as "Identities".

The original unmutated proteins preferably have at least 85%, more preferably at least 90%, still more preferably at least 95% sequence identity to the amino acid sequence of SEQ ID NO:1. The original unmutated proteins are most preferably a protein consisting of the amino acid sequence of SEQ ID NO:1. This protein is a *Candida maltosa*-derived enzyme of the MDR family (WO 08/066,018, abbreviated as RMA hereinbelow). A function of RMA is to catalyze the reduction of a ketone into an optically active alcohol using NADH as a coenzyme. In the case of proteins of the present invention which are designed by introducing amino acid substitution(s) into the protein (RMA) consisting of the amino acid sequence of SEQ ID NO:1, the coenzyme dependency is converted to NADPH dependency from NADH dependency. The principle of the present invention is based on three-dimensional structure modeling of RMA (SEQ ID NO:1).

The term "amino acid residue at a position conformationally equivalent" refers to an amino acid residue which is determined to be at a position equivalent to a particular position in the protein consisting of the amino acid sequence of SEQ ID NO:1 by predicting a three dimensional structure of an original unmutated protein based on its amino acid sequence data, and comparing it with the three-dimensional structure of the protein consisting of the amino acid sequence of SEQ ID NO:1.

The following description illustrates, by way of example, a rational design technique of amino acid substitutions in which the protein of SEQ ID NO:1 is used as an original unmutated protein. The rational design of the three-dimensional structure of RMA can be accomplished by three-dimensional modeling of RMA. The wild-type RMA of SEQ ID NO:1 has not been analyzed for structure by methods such as X-ray crystalline analysis, and thus its three-dimensional structure is still unknown.

Multiple amino acid sequence alignments with enzymes which have amino acid sequence homology to RMA and whose three-dimensional structures are registered in the Protein Data Bank (PDB) are constructed based on the amino acid sequence data of RMA using the program ClustalX (Thompson, J. D. et al., "Nucleic Acid Res." 1994, Vol. 22, 4673-80). Such proteins having high amino acid sequence homology to RMA can be selected by an amino acid sequence homology search among amino acid sequences of proteins registered in PDB using either BLAST (Altschul, S. F. et al., "Nucleic Acid Res." 1997, Vol. 25, 3389-3402) or PSI-BLAST (Shaffer A. A. et al., "Bioinfomatics", 2000, Vol. 164, 88-489).

Next, a three-dimensional structural alignment is performed on these proteins whose three-dimensional structures are known using a three-dimensional graphics program such as Swiss-PDB Viewer (Guex N. et al., "Electrophoresis", 1997, Vol. 18, 2714-2723) and a three-dimensional structure comparison/similar structure search server such as VAST Search (Gibrat J. F. et al., "Curr. Opin. Struct. Biol." 1996, Vol. 6, 377-). The above-mentioned multiple alignments obtained only based on the amino acid sequences are modified based on the similarity between the three-dimensional structures. Based on the resulting sequence alignments, a protein presumed to have a highly similar three-dimensional structure (PDB code: 1LLU) is selected as a template protein for molecular modeling. This template protein is displayed on the program Swiss PDB-Viewer, and altered by substitutions of amino acid residues based on the sequence alignments to match with the amino acid sequence (SEQ ID NO:1) of RMA. The inserted and deleted sites are replaced with the most suitable similar substructures which are searched from PDB, whereby a three-dimensional structure model can be constructed.

Based on this three-dimensional structure model, sites (residues) that are presumed to be significantly involved in the ability to bind to a coenzyme but hardly have an influence on the functions except the coenzyme binding ability are identified in and around a coenzyme binding pocket. Next, a three-dimensional model in which NADH or NADPH is virtually docked is constructed, and free energy calculations using this docked model are performed in accordance with computational chemical techniques to design mutations which reduce the affinity for NADH and increase the affinity for NADPH. Generally, the stability of enzyme (protein)-coenzyme (substrate) complexes can be discussed based on free energy (A. R. Leach, "Molecular Modeling—PRINCIPLES AND APPLICATIONS—", 2004, Chapter 11).

Specifically, a molecular structure model (the framework of the main chain) can be used to calculate the free energy difference observed between the apo form without the coenzyme and the holo form with the coenzyme bound thereto by molecular simulation calculations (energy minimization calculations) based on molecular mechanics. This technique is specifically an applied technique for designing a drug capable of binding to a target protein. Mutations useful for conversion of the coenzyme dependency are particularly characterized in that the LBDD ligand-base free energy difference is advantageous for the apo form when the coenzyme is NADH, and advantageous for the holo form when the coenzyme is NADPH, as compared to the wild-type. Specifically, candidate amino acid mutations are selected by computational screening using the program Shrike (JP 2001-184381 A).

This method makes it possible to identify sites that are important for the coenzyme recognition ability in about 350-residue enzymes of the MDR (medium-chain dehydrogenase/reductase) family, and to select amino acids optimal for the respective sites (and combinations of such sites and optimal amino acids) to achieve the target coenzyme dependency. It is easy to identify sites conformationally equivalent to positions 201, 202, 203, and 206 of SEQ ID NO:1 in enzymes of the MDR (medium-chain dehydrogenase/reductase) family. Specifically, the conformationally equivalent positions can be easily identified based on three-dimensional structure-based amino acid sequence alignment with an amino acid sequence whose three-dimensional structure is known (for example, the amino acid sequence of 1LLU (PDB code) used in the present invention) using a three-dimensional structure comparison/similar structure search server such as VAST Search mentioned above. VAST Search is also available from National Center for Biotechnology Information.

Preferably, the proteins of the present invention are proteins which are classified to the medium-chain dehydrogenase/reductase family, and contain at least one of the following amino acid residues (a) to (d):
(a) Ala or Ser at a position conformationally equivalent to Asp-201 of SEQ ID NO:1;
(b) Arg at a position conformationally equivalent to Lys-202 of SEQ ID NO:1;
(c) Ser at a position conformationally equivalent to Lys-203 of SEQ ID NO:1; and
(d) Lys at a position conformationally equivalent to Ala-206 of SEQ ID NO:1.

More preferably, the proteins are classified to the medium-chain dehydrogenase/reductase family and contain all of the following amino acid residues (e) to (g):
(e) Ser at a position conformationally equivalent to Asp-201 of SEQ ID NO:1;
(f) Arg at a position conformationally equivalent to Lys-202 of SEQ ID NO:1; and
(g) Lys at a position conformationally equivalent to Ala-206 of SEQ ID NO:1.

Introduction of any of the mutations (a) to (d) or introduction of the mutations (e) to (g) converts alcohol dehydrogenases that are dependent on NADH (or NAD+) to be dependent on NADPH (or NADP+).

The mutated proteins preferably have at least 85%, more preferably at least 90%, still more preferably at least 95% sequence identity to the amino acid sequence of SEQ ID NO:1. Specifically, the mutated proteins preferably contain any one of the amino acid sequences of SEQ ID NOs:2 to 8, and more preferably contain the amino acid sequence of SEQ ID NO:2 or 3.

Preferably, the proteins of the present invention have alcohol dehydrogenase activity, and contain at least one of the following amino acid residues (i) to (l):
(i) Asp at a position conformationally equivalent to Asp-201 of SEQ ID NO:1;
(j) Lys at a position conformationally equivalent to Lys-202 of SEQ ID NO:1;
(k) Lys at a position conformationally equivalent to Lys-203 of SEQ ID NO:1; and
(l) Ala at a position conformationally equivalent to Ala-206 of SEQ ID NO:1.

Introduction of any of the mutations (i) to (l) converts alcohol dehydrogenases that are dependent on NADPH (or NADP+) to those dependent on NADH(NAD+).

Preferably, the proteins of the present invention have decreased oxidative (or reductive) activity (hereinafter, abbreviated as oxidative/reductive activity) for a coenzyme for which their original unmutated proteins show high oxidative/reductive activity. Or, the proteins preferably have increased oxidative/reductive activity for a coenzyme for which their original unmutated proteins show only low oxidative/reductive activity (or do not show activity at all). More preferably, the proteins of the present invention have both of these characteristics.

The term "coenzyme oxidative/reductive activity ratio" refers to a value determined by dividing the oxidative/reductive activity of a mutated protein for a coenzyme on which the mutated protein is dependent by the oxidative/reductive activity of the original unmutated protein for the other coenzyme on which the original unmutated enzyme is dependent. For example, in the case of RMA, its coenzyme oxidative/reductive activity is expressed as an oxidative activity ratio (NADPH/NADH). The coenzyme oxidative/reductive activity is preferably not less than 1, more preferably not less than 5, and still more preferably not less than 10. In order to achieve selective oxidation/reduction of only either of the coenzymes on which the mutated protein is dependent, a strict level of the coenzyme selectivity is required. For such strict selectivity, the ratio is more preferably not less than 20, and for stricter coenzyme selectivity, the ratio is most preferably not less than 30. For example, in the case where two reactions using enzymes that are dependent on different nicotinamide coenzymes are performed at the same time, strict selectivity is generally required. It should be noted that the coenzyme oxidative/reductive activity ratio of the original unmutated enzymes is at most about 0.1. Enzymes having a higher ratio than this level are considered to be dependent on both the coenzymes.

In the case where the coenzyme oxidative/reductive activity of RMA is determined, the enzyme activity capable of oxidizing 1 μmol of NADPH (or NADH) to NADP+ (NAD+) in one minute is defined as 1 Unit. The oxidative/reductive activities of the original unmutated enzyme and a mutated enzyme are determined using the same reaction solution composition and the same enzyme concentration. In the case where the coenzyme oxidative/reductive activity of RMA is determined, preferred conditions are, but not limited to, ventilation agitation for a certain period of time at a pH of 4.0 to 10.0 and a constant temperature of 4° C. to 80° C. The conditions may be set based on a consideration of properties of a coenzyme regeneration enzyme used together. The proteins of the present invention maintain the original functions, such as substrate specificity, except their converted coenzyme dependency.

DNAs of the present invention contain a base sequence encoding a protein of the present invention. The DNAs may be any DNAs as long as they can be transfected into host cells in the manner described below, and express a protein of the present invention therein. The DNAs may contain any untranslated regions. Once a protein is designed, a DNA of the present invention can be obtained by obtaining an original unmutated DNA from an organism that is a source of the original unmutated protein in a manner known to those skilled in the art, and introducing mutation(s) into this DNA.

Site-directed mutanogenesis to a DNA encoding a wild-type enzyme of the MDR family can be accomplished by recombinant DNA technology, PCR, or the like. In the case where appropriate restriction enzyme recognition sequences are present on both sides of a mutagenesis target site in a wild-type enzyme gene, introduction of a mutation(s) by recombinant DNA technology can be accomplished by cassette mutagenesis in which a region containing the mutagenesis target site is removed by cleaving these restriction enzyme recognition sequences with the restriction enzymes, and then a DNA fragment containing the mutation only at the target site, prepared by a method such as chemical synthesis, is inserted. Alternatively, site-directed mutagenesis by PCR can be accomplished as follows: one side of a wild-type coding DNA is amplified using a mutation primer containing a target mutation at a mutagenesis target site of the wild-type coding gene and an amplification primer containing a sequence at one end of the gene without mutations; the other side is amplified using another mutation primer having a complementary sequence to the former mutation primer and another amplification primer containing a sequence at the other end of the gene without mutations; and these two amplified fragments are annealed and then subjected to PCR with the two amplification primers. Other than the recombinant DNA technology and PCR, chemical synthesis can be used to prepare a DNA encoding a mutated amino acid sequence.

Examples of the DNAs encoding a protein of the present invention which are obtainable as described above include DNAs containing any one of the base sequences of SEQ ID NOs:25 to 31.

Other examples of the DNAs of the present invention include DNAs which are capable of hybridizing with a DNA containing a base sequence complementary to any of the base sequences of SEQ ID NOs:25 to 31 under stringent conditions, and contain a base sequence encoding a protein having oxidoreductase activity.

Further examples of the DNAs of the present invention include DNAs having at least 85% sequence identity to any of the base sequences of SEQ ID NOs:25 to 31, and containing a base sequence encoding a protein having oxidoreductase activity.

The expression "DNAs which are capable of hybridizing with a DNA containing a base sequence complementary to any of the base sequences of SEQ ID NOs:25 to 31 under stringent conditions, and contain a base sequence encoding a protein having oxidoreductase activity" herein means DNAs encoding a protein having oxidoreductase activity which are obtainable by techniques such as colony hybridization, plaque hybridization, and southern hybridization using a DNA containing a base sequence complementary to any of the base sequences of SEQ ID NOs:25 to 31 as a probe under stringent conditions.

The hybridization can be accomplished, for example, by a method disclosed in Molecular Cloning, A laboratory manual, second edition (Cold Spring Harbor Laboratory Press, 1989). The expression "DNAs capable of hybridizing . . . under stringent conditions" as used herein means, for example, DNAs obtained by hybridization using a filter with a colony- or plaque-derived DNA immobilized thereon in the presence of 0.7 to 1.0 M NaCl at 65° C., and washing the filter at 65° C. with a 2×SSC solution (the composition of a 1×SSC solution is as follows: 150 mM sodium chloride; and 15 mM sodium citrate). Preferred are DNAs obtained by washing at 65° C. with a 0.5×SSC solution, more preferred are DNAs obtained by washing at 65° C. with a 0.2×SSC solution, and still more preferred are DNAs obtained by washing at 65° C. with a 0.1×SSC solution.

The hybridization conditions are not limited to those described above. Several factors, such as temperature and salt concentration, are thought to affect the stringency of hybridization, and those skilled in the art can select appropriate conditions for such factors to achieve the optimal stringency.

As DNAs hybridizable under the above-mentioned conditions, mention may be made of DNAs having at least 85%, preferably at least 90%, more preferably at least 95% sequence identity to any of the base sequences of SEQ ID NOs:25 to 31. These DNAs are included in the scope of the DNAs defined above as long as they encode a polypeptide having oxidoreductase activity.

The term "sequence identity (%)" as used herein refers to a value determined by optimally aligning two DNAs to be compared, dividing the number of corresponding sites with the same nucleic acid base (for example, A, T, C, G, U, or I) in both of the sequences by the total number of bases compared, and multiplying the result by 100.

Vectors of the present invention are obtainable by incorporating a DNA of the present invention into an adequate vector. Empty vectors to which a DNA is to be introduced are not limited at all provided that they are capable of autonomous replication in host cells. Examples of such vectors include plasmid DNAs and phage DNAs. Examples of vectors usable with *Escherichia coli* host cells include plasmid DNAs such as pBR322, pUC18, and pBluescript II, and phage DNAs such as EMBL3, M13, and λgt11. Examples of vectors usable with yeast host cells include YEp13 and YCp50. Examples of vectors usable with plant host cells include pBI121 and pBI101. Examples of vectors usable with animal host cells include pcDNAI.

Transformants of the present invention are obtainable by transformation of host cells with a vector described above. Any host organisms can be used provided that they can be transformed with an expression vector containing a coding DNA, and the incorporated coding DNA can express a protein. Examples of usable microorganisms include bacteria that are used as hosts of known host-vector systems, such as bacteria of *Escherichia, Bacillus, Pseudomonas, Serratia, Brevibacterium, Corynebacterium, Streptococcus*, and *Lactobacillus*; actinomycetes that are used as hosts of known host-vector systems, actinomycetes of *Rhodococcus* and *Streptomyces*; yeasts that are used as hosts of known host-vector systems, such as yeasts of *Saccharomyces, Kluyveromyces, Schizosaccharomyces, Zygosaccharomyces, Yarrowia, Trichosporon, Rhodosporidium, Pichia*, and *Candida*; and molds that are used as hosts of known host-vector systems, such as molds of *Neurospora, Aspergillus, Cephalosporium*, and *Trichoderma*. In addition to the above microorganisms, a variety of plant and animal host-vector systems have been developed, and in particular, systems for expressing large quantities of foreign proteins in insects such as silkworms or in rapeseed, corn, potatoes and other plants have been developed. These systems can also be used favorably. Of these, bacteria are preferred in terms of the introduction efficiency and expression efficiency, and *E. coli* is more preferred.

Transfection of bacterial cells with a recombinant DNA can be accomplished by, for example, a method using calcium ions or an electroporation method. Transfection of yeast cells with a recombinant DNA can be accomplished by, for example, an electroporation method, a spheroplast method, or a lithium acetate method. Transfection of plant cells with a recombinant DNA can be accomplished by, for example, an *Agrobacterium* infection method, a particle gun method, or a polyethylene glycol method. Transfection of animal cells with a recombinant DNA can be accomplished by, for example, an electroporation method or a calcium phosphate method.

Cultures of the present invention are obtainable by culturing a transformant described above. Cultures containing proteins of the present invention are obtainable by culturing transformants in media to produce and accumulate proteins in the cultured cells or in the culture supernatants, and collecting the enzyme variants.

The transformants can be cultured in accordance with a common method for culturing host cells. Examples of media for culturing transformants of bacterial hosts such as *E. coli* include complete media and synthetic media such as LB media, TB media and M9 media. Specifically, cells are aerobically cultured at a temperature of 20° C. to 40° C. to accumulate an enzyme variant of the present invention in the cells, and the enzyme variant is then recovered. The enzyme variant is purified by collecting the culture obtained in the manner as described above by centrifugation, disrupting cells with a sonicator or the like, and then performing any one or an appropriate combination of techniques such as affinity chromatography, cation or anion exchange chromatography and gel filtration chromatography. Examples of techniques to confirm whether a purified substance is a target enzyme include common techniques such as SDS polyacrylamide gel electrophoresis and Western blotting. The purification of a culture of a transformant is a process for removing unnecessary substances other than the target enzyme without losing the activity of the enzyme. The resulting product containing the enzyme is referred to as a purified product. Such a purified product is obtainable, for example, in the form of a cell-free extract by disrupting cells, or in the form of an enzyme solution by purification, or in the form of a freeze-dried product of the enzyme solution.

Proteins obtained by introducing at least one amino acid substitution selected from the substitutions (a) to (d) into proteins having alcohol dehydrogenase activity have increased dependency on NADPH and decreased dependency on NADH compared to their original proteins before the introduction of substitution(s). Therefore, these proteins can be used to convert reduced nicotinamide adenine dinucleotide phosphate (NADPH) into oxidized nicotinamide adenine dinucleotide phosphate (NADP+).

This reaction is a static reaction. This means that these proteins can also be used to convert oxidized nicotinamide adenine dinucleotide phosphate (NADP+) into reduced nicotinamide adenine dinucleotide phosphate (NADPH).

Proteins obtained by introducing at least one amino acid substitution selected from the substitutions (i) to (l) into proteins having alcohol dehydrogenase activity have increased dependency on NADH and reduced dependency on NADPH than their original proteins before the introduction of substitution(s). Accordingly, the proteins of the present invention can be used to convert reduced nicotinamide adenine dinucleotide (NADH) into oxidized nicotinamide adenine dinucleotide (NAD+).

This reaction is a static reaction. This means that these proteins can also be used to convert oxidized nicotinamide adenine dinucleotide (NAD+) into reduced nicotinamide adenine dinucleotide (NADH).

In order to increase the production of optically active alcohols, a coenzyme regeneration system may be incorporated in the reaction systems involving the proteins of the present invention.

When such a coenzyme regeneration system is used to act on oxidized nicotinamide adenine dinucleotide phosphate (NADP+) produced using a protein of the present invention or oxidized nicotinamide adenine dinucleotide (NAD+) produced using a protein of the present invention, reduced nicotinamide adenine dinucleotide phosphate (NADPH) or reduced nicotinamide adenine dinucleotide (NADH) are produced. The coenzyme regeneration system is an enzyme having activity for reducing the oxidized form of either coenzyme, and specific examples include glucose dehydrogenase (GDH), formate dehydrogenase (FDH), lactate dehydrogenase (LDH), and malate dehydrogenase (MDH).

Likewise, when a coenzyme regeneration system is used to act on reduced nicotinamide adenine dinucleotide phosphate (NADPH) produced using a protein of the present invention or reduced nicotinamide adenine dinucleotide (NADH) produced using a protein of the present invention, oxidized nicotinamide adenine dinucleotide phosphate (NADP+) or oxidized nicotinamide adenine dinucleotide (NAD+) can be produced. Such a coenzyme regeneration system is an enzyme having activity for oxidizing the reduced form of either coenzyme. Specific examples include glucose dehydrogenase (GDH), formate dehydrogenase (FDH), lactate dehydrogenase (LDH), and malate dehydrogenase (MDH).

The production of reduced nicotinamide adenine dinucleotide phosphate (NADPH), oxidized nicotinamide adenine dinucleotide phosphate (NADP+), reduced nicotinamide adenine dinucleotide (NADH) or oxidized nicotinamide adenine dinucleotide (NAD+) can be accomplished by using the transformants or cultures of the transformants.

EXAMPLES

Amino acid substitutions are each represented herein by an amino acid residue of the wild-type or non-mutated type, followed by the position number of the substitution, followed by an amino acid residue introduced by the substitution. For example, a substitution of Ala for Asp at position 201 is represented by D201A.

Example 1

Preparation of Recombinant Vector Containing RMA Variant Gene and Preparation of Recombinant E. coli In order to obtain *E. coli* cells capable of expressing variants of the *Candida maltosa*-derived enzyme of the MDR (medium-chain dehydrogenase/reductase) family (WO 08/066,018, abbreviated as RMA hereinbelow), expression plasmids for the variants were prepared using pNCM vector (RMA wild-type expression plasmid) described in the same literature.

Specifically, mutations were introduced by quick change mutagenesis using two synthetic primers designed for introduction of mutations at desired sites and the pNCM vector as a template, and thus recombinant plasmids containing RMA variant genes were obtained. The quick change mutagenesis was carried out using QuickChange Site-Directed Mutagenesis Kit (Stratagene) in accordance with the manufacturer's protocol. Specifically, first, an expression plasmid for an RMA variant containing the mutation A206K was prepared by quick change mutagenesis using pNCM (SEQ ID NO:9) as a template DNA, and two synthetic primers of SEQ ID NOs: 10 and 11. The obtained expression plasmid had the coding DNA sequence of SEQ ID NO:12. The quick change mutagenesis is a mutation introducing technique in which transformation is included in its protocol. In this example, this technique was used to transform *E. coli* HB101 (Takara) into a recombinant *E. coli*. Then, quick change mutagenesis was performed in the same manner as described above using an expression plasmid containing a coding DNA of SEQ ID NO:9 (wildtype) or SEQ ID NO:12 (variant K206R) as a template and two of synthetic primers of SEQ ID NOs:13 to 22. Thus, expression plasmids respectively encoding the amino acid sequences of SEQ ID NOs:2 to 8 and recombinant *E. coli* transformants were prepared (the coding DNA sequences of these expression plasmids are shown as SEQ ID NOs:25 to 31, respectively). Table 1 shows all combinations of the amino acid sequences and coding DNA sequences of the respective variant expression plasmids, and SEQ ID NOs of the template DNA plasmids and mutation primers used for the preparation in this experiment.

Table of combinations of variant expression plasmids and SEQ ID NOs

TABLE 1

| | Amino acid sequence | Coding DNA | Template DNA | Mutation primer |
|---|---|---|---|---|
| Wild | 1 | 9 | — | — |
| A206K(as template) | — | 12 | 9 | 10, 11 |
| D201S/K202R/A206K | 2 | 25 | 12 | 13, 14 |
| D201A/K202R/A206K | 3 | 26 | 12 | 15, 16 |
| D201S/K202R/K203S/A206K | 4 | 27 | 12 | 17, 18 |
| D201A/K202R/K203S/A206K | 5 | 28 | 12 | 19, 20 |
| D201S/K203S/A206K | 6 | 29 | 12 | 21, 22 |

TABLE 1-continued

| | Amino acid sequence | Coding DNA | Template DNA | Mutation primer |
|---|---|---|---|---|
| D201A/K203S/A206K | 7 | 30 | 12 | 23, 24 |
| D201S/K202R | 8 | 31 | 9 | 13, 14 |

Example 2

Expression of RMA Variant Using Recombinant E. coli and Preparation of Cell-Free Extract The recombinant *E. coli* HB101 transformants prepared in Example 1 were respectively inoculated on semisynthetic media (glycerin 1.5% (w/v), yeast extract 0.3% (w/v), $Na_2HPO_4$ 0.6% (w/v), $KH_2PO_4$ 0.3% (w/v), NaCl 0.2% (w/v), $MgSO_4 \cdot 7H_2O$ 0.5% (w/v), 100 µg/ml ampicillin, pH 7.2), and grown at 30° C. for 60 hours. Cells in the cultures were collected, and the supernatants were removed from the cultures. Then, the cells from each culture were suspended in a buffer (100 mM potassium phosphate, pH 7.0) in an amount equivalent to that of the medium, and disrupted ultrasonically. The resulting suspensions were then centrifuged, and the supernatants were removed. In this manner, cell-free extracts were obtained.

Example 3

Measurement of Activity for Oxidizing Pyridine Nucleotide

The cell-free extracts containing the RMA variants prepared in Example 2 were each added to a solution shown below which contained a ketone compound as a reaction substrate, and the resulting solutions were measured for NADPH oxidative activity and NADH oxidative activity.

A 0.05-mL portion of each enzyme solution was added to 0.95 mL of a reaction solution containing 100 mM potassium phosphate buffer (pH 7.0), 5 mM NADPH, and 0.6 M 2-butanone (methyl ethyl ketone, MEK), and the resulting solution was monitored for a decrease in the absorption at 340 nm at a constant temperature (25° C.). The enzyme activity capable of oxidizing 1 µmol of NADPH to NADP+ in one minute under the above conditions was defined as 1 Unit. For convenience of the measurement, the cell-free extracts were optionally diluted with the potassium phosphate buffer to show a decrease in the absorption, as measured at 340 nm for 1 minute, of about 0.1 to 0.4, and these diluted solutions were used as enzyme solutions. The enzyme activity was calculated considering the dilution ratio. To determine the enzyme activity capable of oxidizing NADH to NAD+, the same procedures as described above were performed except that NADPH used in the reaction solutions was replaced with NADH.

Table 2 shows the results. The oxidative activity is expressed as a relative value (%) to that of the wild-type RMA. Although the original unmutated protein showed high activity for oxidizing NADH, the NADH oxidative activity of the RMA variants decreased to about 1/50 to 1/500. In addition, although the original unmutated protein showed low activity for oxidizing NADPH, the NADPH oxidative activities of the variants increased about 10- to 50-fold. The oxidative activity ratio (NADPH/NADH) increased by the mutations about 100 to 2000-fold from about 0.003 of the original unmutated protein.

Coenzyme Oxidative Activity of RMA Variant

TABLE 2

| RMA Variant Mutation | SEQ ID NO | Coenzyme oxidative activity (relative value %) NADPH | Coenzyme oxidative activity (relative value %) NADH | Oxidative activity ratio NADPH/NADH |
|---|---|---|---|---|
| Wild(Comparative Example 1) | 1 | 100 | 100 | 0.0028 |
| D201S/K202R/A206K | 2 | 6530 | 0.41 | 44.0 |
| D201A/K202R/A206K | 3 | 2530 | 0.19 | 37.0 |
| D201S/K202R/K203S/A206K | 4 | 3260 | 0.31 | 29.0 |
| D201A/K202R/K203S/A206K | 5 | 3620 | 0.64 | 16.0 |
| D201S/K203S/A206K | 6 | 3260 | 1.9 | 4.7 |
| D201A/K203S/A206K | 7 | 1090 | 1.7 | 1.8 |
| D201S/K202R | 8 | 1090 | 1.2 | 2.4 |

Example 4

Construction of NADPH Regeneration Cycle in Ketone Reduction by RMA Variant 2-Butanone was reduced to (S)-2-butanol (S-MEH) using the RMA variant (D201S/K202R/A206K, SEQ ID NO:2). This reaction was accompanied by oxidation of NADPH to NADP+. To this reaction system, *Lactobacillus*-derived NADP+-dependent GDH (GDHLP, WO 09/041,415) and its substrate glucose were added to regenerate NADPH at the same time. FIG. 1 shows a scheme of the elementary reactions (NADPH regeneration cycle). The enzyme solution of *Lactobacillus*-derived NADP+-dependent GDH was prepared in the manner described in WO 09/041,415.

The composition of the reaction solution was as follows.

TABLE 3

| | |
|---|---|
| GDHLP (561 U/mL) | 29.31 g |
| Glucose | 4.40 g (1.1 equivalents to MEK) |
| 2-Butanone (MEK) | 1.52 g (loaded amount 4%) |
| NADP+ | 0.034 g (0.002 equivalents to MEK) |
| 15% $H_2SO_4$ | 0.62 g |
| RMA variant (220 U/mL) | 10.29 g |
| Total | 46.17 g |

The materials were added in the order stated above, and reacted at 30° C. and pH 5.5 (the minimum pH was maintained by a pH stat with NaOH) for 35 hours. By-products were analyzed by gas chromatography. The gas chromatography device used was SHIMADZU GC-14B (Shimadzu Corp.). The conversion ratio to S-MEH was analyzed using TC-WAX (GL Sciences Inc.), and the optical purity of S-MEH was analyzed using Cyclodex-β (Agilent Technologies).

The analyses were performed under the following conditions.

[Conversion Ratio to S-MEH: Conditions of Gas Chromatography Analysis]
Column: TC-WAX (60 m×0.25 mm)
Detection: FID
Hydrogen: 50 kPa
Column temperature: 50° C.
Charging temperature: 200° C.
Detection temperature: 200° C.

Figure 2:
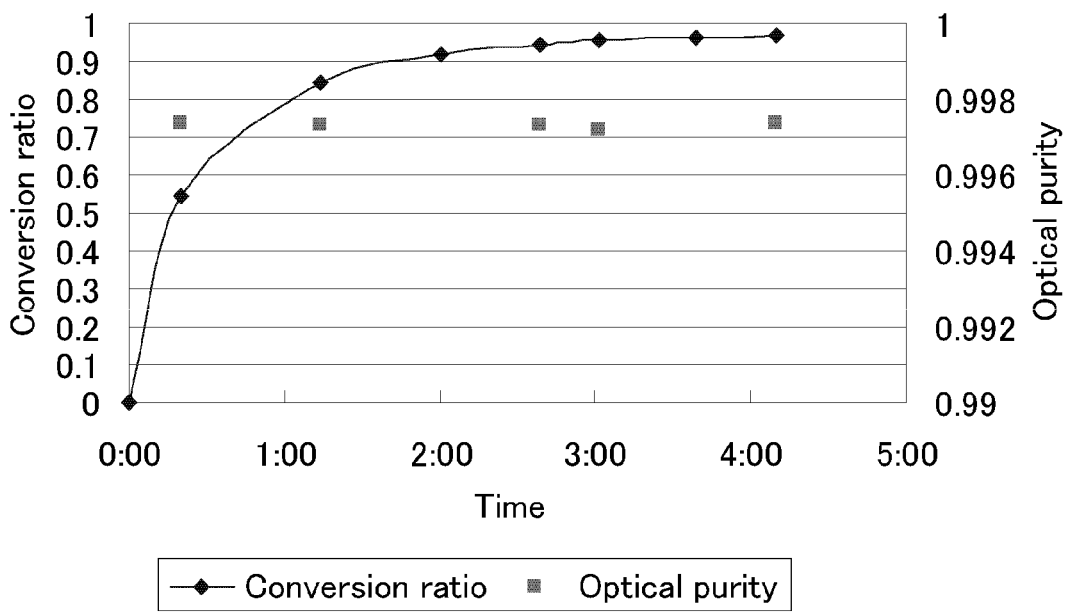
FIG. 2 is a graph showing the results of analyses of the conversion ratio and optical purity of an optically active alcohol obtained by the reactions of Example 4 of the present invention.

Carrier gas: helium (300 kPa)
Elution time: 2-butanone (MEK) 4.8 minutes
  2-butanol (MEH) 7.1 minutes
[Optical Purity of S-MEH: Conditions of Gas Chromatography Analysis]
Column: Cyclodex-8 (60 m×0.25 mm)
Detection: FID
Hydrogen: 50 kPa
Column temperature: 35° C.
Charging temperature: 150° C.
Detection temperature: 150° C.
Carrier gas: helium (300 kPa)
Elution time: 2-butanone (MEK) 6.5 minutes
  (R)-2-butanol (R-MEH) 11.0 minutes
  (S)-2-butanol (S-MEH) 11.4 minutes FIG. 2 shows the results of the analyses. The conversion ratio reached 97.1% after 4 hours from the start of reaction, and the optical purity at the time was 99.7%. The results revealed that the use of the RMA variants obtained by the present invention makes it possible to use the *Lactobacillus*-derived NADP+-dependent GDH having good properties as a coenzyme regeneration system, and actually resulted in production of a target optically active alcohol by using expensive NADPH only in a catalyst quantity.

Comparative Example 1

Wild-Type RMA

As for the wild-type RMA (SEQ ID NO:1), recombinant *E. coli* cells were prepared by transfecting *E. coli* HB101 (Takara) with the expression plasmid (pNCM vector) that was used above as a template. A cell-free extract was prepared in the same manner as in Example 2, and measured for activity for oxidizing the pyridine nucleotides in the same manner as in Example 3. The results are shown in Table 2.

The invention claimed is:

1. A protein of medium-chain dehydrogenase/reductase family, containing at least one of following amino acid residues (a) to (d):

(a) Ala at a position conformationally equivalent to Asp-201 of SEQ ID NO: 1;

(b) Arg at a position conformationally equivalent to Lys-202 of SEQ ID NO: 1;

(c) Ser at a position conformationally equivalent to Lys-203 of SEQ ID NO: 1; or (d) Lys at a position conformationally equivalent to Ala-206 of SEQ ID NO: 1.

2. The protein according to claim 1, wherein the protein comprises an amino acid sequence having at least 85% sequence identity to the amino acid sequence of SEQ ID NO: 1.

3. The protein according to claim 1 or 2, wherein the protein comprises an amino acid sequence obtained by introducing at least one of the following mutations (e) to (h) into the amino acid sequence of SEQ ID NO: 1:

(e) a substitution of Ala for Asp-201;
(f) a substitution of Arg for Lys-202;
(g) a substitution of Ser for Lys-203; or
(h) a substitution of Lys for Ala-206.

4. The protein according to claim 1, Wherein the protein comprises any one of amino acid sequences of SEQ ID NOs: 2 to 8.

5. A DNA, comprising a base sequence encoding a protein of medium-chain dehydrogenase/reductase family, containing at least one of following amino acid residues (a) to (d):
   (a) Ala at a position conformationally equivalent to Asp-201 of SEQ ID NO: 1;
   (b) Arg at a position conformationally equivalent to Lys-202 of SEQ ID NO: 1;
   (c) Ser at a position conformationally equivalent to Lys-203 of SEQ ID NO: 1; or
   (d) Lys at a position conformationally equivalent to Ala-206 of SEQ ID NO: 1.

6. A DNA, selected from the group consisting of:
   (A) a DNA comprising any one of base sequences of SEQ ID NOs: 25 to 31;
   (B) a DNA which is capable of hybridizing with a DNA comprising a base sequence complementary to any one of base sequences of SEQ ID NOs: 25 to 31 under stringent conditions, and comprises a base sequence encoding a protein having oxidoreductase activity, Wherein the stringent conditions are hybridization using a filter with a colony- or plaque-derived DNA immobilized thereon in the presence of 0.7 to 1.0 M NaCl at 65° C., and washing the filter at 65° C. with a 2×SSC solution, with the proviso that a DNA of SEQ ID NO: 9 is excluded; and
   (C) a DNA having at least 85% sequence identity to any one of base sequences of SEQ ID NOs: 25 to 31, and comprising a base sequence encoding a protein having oxidoreductase activity, with the proviso that a DNA of SEQ ID NO: 9 is excluded.

7. A vector, comprising the DNA according claim 5 or 6.

8. A transformant, obtained by transformation of a host cell with the vector according to claim 7.

9. A culture of the transformant according to claim 8.

10. A method for producing oxidized nicotinamide adenine dinucleotide phosphate, the method comprising allowing the protein according to claim 1 to react with and to convert reduced nicotinamide adenine dinucleotide phosphate into oxidized nicotinamide adenine dinucleotide phosphate.

11. A method for producing reduced nicotinamide adenine dinucleotide phosphate, the method comprising:
   providing the protein according to claim 1 to react with and to convert oxidized nicotinamide adenine dinucleotide phosphate into reduced nicotinamide adenine dinucleotide phosphate.

12. A method for producing reduced nicotinamide adenine dinucleotide phosphate, the method comprising allowing a reductase to act on the oxidized nicotinamide adenine dinucleotide phosphate obtained by the method according to claim 10.

13. A method for producing oxidized nicotinamide adenine dinucleotide phosphate, the method comprising allowing an oxidase to act on the reduced nicotinamide adenine dinucleotide phosphate obtained by the method according to claim 11.

14. The production method according claim 10, which further comprises using a transformant obtained by transformation of a host cell with a vector comprising a DNA encoding the protein of claim 1.

15. The production method according to claim 10, which comprises using a transformant obtained by transformation of a host cell with a vector encoding said protein with the further proviso that the protein is encoded by a DNA selected from the group consisting of:
   (A) a DNA comprising any one of base sequences of SEQ ID NOs: 25 to 31;
   (B) a DNA which is capable of hybridizing with a DNA comprising a base sequence complementary to any one of base sequences of SEQ ID NOs: 25 to 31 under stringent conditions, and comprises a base sequence encoding a protein having oxidoreductase activity, wherein the stringent conditions are hybridization using a filter with a colony- or plaque-derived DNA immobilized thereon in the presence of 0.7 to 1.0 M NaCl at 65° C., and washing the filter at 65° C. with a 2×SSC solution; and
   (C) a DNA having at least 85% sequence identity to any one of base sequences of SEQ ID NOs: 25 to 31, and comprising a base sequence encoding a protein having oxidoreductase activity,
   wherein (A), (B), and (C) encode the protein of medium-chain dehydrogenase/reductase family containing at least one of following amino acid residues (a) to (d):
   (a) Ala at a position conformationally equivalent to Asp-201 of SEQ ID NO: 1;
   (b) Arg at a position conformationally equivalent to Lys-202 of SEQ ID NO: 1;
   (c) Ser at a position conformationally equivalent to Lys-203 of SEQ ID NO: 1; or
   (d) Lys at a position conformationally equivalent to Ala-206 of SEQ ID NO: 1.

16. The protein according to claim 1, wherein the protein comprises:
   (a) Ala at a position conformationally equivalent to Asp-201 of SEQ ID NO: 1.

17. The protein according to claim 1, wherein the protein comprises:
   (b) Arg at a position conformationally equivalent to Lys-202 of SEQ ID NO: 1.

18. The protein according to claim 1, wherein the protein comprises:
   (c) Ser at a position conformationally equivalent to Lys-203 of SEQ ID NO: 1.

19. The protein according to claim 1, wherein the protein comprises:
   (d) Lys at a position conformationally equivalent to Ala-206 of SEQ ID NO: 1.

20. The protein according to claim 1, wherein the protein comprises SEQ ID NO:1 except that it contains two of the following amino acid substitutions at amino acid positions 201, 202, 203, and 206 of SEQ ID NO 1:
   (a) Ala at a position conformationally equivalent to Asp-201 of SEQ ID NO: 1;
   (b) Arg at a position conformationally equivalent to Lys-202 of SEQ ID NO: 1;
   (c) Ser at a position conformationally equivalent to Lys-203 of SEQ ID NO: 1; or
   (d) Lys at a position conformationally equivalent to Ala-206 of SEQ ID NO: 1.

21. The protein according to claim 1, wherein the protein comprises SEQ ID No:1 except that it contains three of the following amino acid substitutions at amino acid positions 201, 202, 203, and 206 of SEQ ID NO 1:
   (a) Ala at a position conformationally equivalent to Asp-201 of SEQ ID NO: 1;

(b) Arg at a position conformationally equivalent to Lys-202 of SEQ ID NO: 1;
(c) Ser at a position conformationally equivalent to Lys-203 of SEQ ID NO: 1; or
(d) Lys at a position conformationally equivalent to Ala-206 of SEQ ID NO: 1.

22. The protein according to claim 1, wherein the protein comprises SEQ ID NO:1 except that it contains four of the following amino acid substitutions at amino acid positions 201, 202, 203, and 206 of SEQ ID NO 1:
(a) Ala at a position conformationally equivalent to Asp-201 of SEQ ID NO: 1;
(b) Arg at a position conformationally equivalent to Lys-202 of SEQ ID NO: 1;
(c) Ser at a position conformationally equivalent to Lys-203 of SEQ ID NO: 1; or
(d) Lys at a position conformationally equivalent to Ala-206 of SEQ ID NO: 1.

23. The production method according to claim 15, wherein (A), (B), and (C) encode the protein of medium-chain dehydrogenase/reductase family containing two to four of the following amino acid residues (a) to (e):
(a) Ala at a position conformationally equivalent to Asp-201 of SEQ ID NO: 1;
(b) Arg at a position conformationally equivalent to Lys-202 of SEQ ID NO: 1;
(c) Ser at a position conformationally equivalent to Lys-203 of SEQ ID NO: 1; or
(d) Lys at a position conformationally equivalent to Ala-206 of SEQ ID NO: 1.

* * * * *